USO12048487B2

United States Patent
Amit et al.

(10) Patent No.: US 12,048,487 B2
(45) Date of Patent: Jul. 30, 2024

(54) SYSTEMS AND METHODS FOR IMPROVING CARDIAC ABLATION PROCEDURES

(71) Applicant: Biosense Webster (Israel) Ltd., Yokneam (IL)

(72) Inventors: Mati Amit, Yokneam (IL); Benny Dilmoney, Yokneam (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 915 days.

(21) Appl. No.: 16/864,879

(22) Filed: May 1, 2020

(65) Prior Publication Data
US 2020/0352652 A1 Nov. 12, 2020

Related U.S. Application Data

(60) Provisional application No. 62/843,877, filed on May 6, 2019.

(51) Int. Cl.
G09B 23/30 (2006.01)
A61B 18/00 (2006.01)
A61B 34/10 (2016.01)
G06V 10/764 (2022.01)
G09B 23/28 (2006.01)
(Continued)

(52) U.S. Cl.
CPC ............ *A61B 34/10* (2016.02); *A61B 18/00* (2013.01); *G06V 10/764* (2022.01); *G09B 23/28* (2013.01); *A61B 2017/00221* (2013.01); *A61B 2018/00351* (2013.01); *A61B 2018/00577* (2013.01); *A61B 18/1492* (2013.01); *A61B 2034/105* (2016.02);
(Continued)

(58) Field of Classification Search
CPC ................................ G09B 23/28; G09B 23/30
See application file for complete search history.

(56) References Cited

U.S. PATENT DOCUMENTS 9,298,884 B1 * 3/2016 Ahmad ................ G06F 3/0484
11,304,644 B2 * 4/2022 Lu ............................ A61B 5/327
(Continued)

FOREIGN PATENT DOCUMENTS

WO WO2018130976 A1 7/2018

OTHER PUBLICATIONS

European Search Report for Corresponding EPA No. 20172905.0 dated Jan. 19, 2021.

*Primary Examiner* — Kurt Fernstrom
(74) *Attorney, Agent, or Firm* — VOLPE KOENIG

(57) ABSTRACT

A plurality of systems and methods for improving a cardiac ablation procedure are disclosed. The systems and methods include a cloud server that includes a database containing information about previously performed cardiac ablations, a local server that is communicatively coupled to the cloud server via first network, and a surgical system that is communicatively coupled to the local server via second network. The cloud server is configured to receive, via the local server, electrical and anatomical data of a heart of a patient from the surgical system, perform a comparison of the electrical and anatomical data of the heart to the database information, generate a surgical treatment plan for the heart based on the comparison, wherein the surgical treatment plan includes a grid of the heart, and transmit, via the local server, the surgical treatment plan to the surgical system.

9 Claims, 30 Drawing Sheets

(51) Int. Cl.
   *A61B 17/00*      (2006.01)
   *A61B 18/14*      (2006.01)
   *A61B 34/00*      (2016.01)
   *A61B 90/00*      (2016.01)

(52) U.S. Cl.
   CPC ... *A61B 2034/256* (2016.02); *A61B 2090/365* (2016.02)

(56) References Cited

U.S. PATENT DOCUMENTS

| | | | |
|---|---|---|---|
| 2002/0087086 A1 | 7/2002 | Stoycos | |
| 2003/0031993 A1* | 2/2003 | Pugh | G09B 23/34 |
| | | | 434/262 |
| 2010/0167249 A1* | 7/2010 | Ryan | G09B 23/285 |
| | | | 434/267 |
| 2012/0282583 A1* | 11/2012 | Thaler | G09B 23/30 |
| | | | 434/267 |
| 2013/0197881 A1* | 8/2013 | Mansi | A61B 5/0044 |
| | | | 703/2 |
| 2013/0237811 A1* | 9/2013 | Mihailescu | A61B 34/20 |
| | | | 600/407 |
| 2016/0070436 A1 | 3/2016 | Thomas | |
| 2016/0314710 A1* | 10/2016 | Jarc | G09B 23/285 |
| 2016/0314716 A1* | 10/2016 | Grubbs | G09B 23/306 |
| 2017/0027649 A1 | 2/2017 | Kiraly | |
| 2017/0185740 A1* | 6/2017 | Seegerer | A61B 6/5235 |
| 2017/0330487 A1* | 11/2017 | Harlev | G06F 3/04845 |
| 2018/0090029 A1 | 3/2018 | Fisher | |
| 2019/0340956 A1* | 11/2019 | Lindkvist | G09B 23/30 |
| 2019/0380792 A1* | 12/2019 | Poltaretskyi | G06N 3/08 |

* cited by examiner

SYSTEMS AND METHODS FOR IMPROVING CARDIAC ABLATION PROCEDURES

FIELD OF INVENTION

The present application provides systems, apparatuses, and methods for improving cardiac ablation procedures.

BACKGROUND

Cardiac ablation is a surgical procedure that treats abnormal heart rhythms of a patient by scaring or destroying tissue in the patient's heart. Cardiac ablation is often used to treat cardiac arrhythmias such as atrial fibrillation, atrial flutter, supraventricular tachycardias, and Wolff-Parkinson-White syndrome. The cardiac ablation can prevent the abnormal heart rhythms from moving through the heart. In a cardiac ablation procedure, electrical measurements of the heart are made using catheters. Based on the measurements, a surgeon uses heat (radiofrequency), extreme cold (cryoablation), or lasers are used to destroy the areas of the heart where an electrical anomaly is occurring.

Traditional cardiac ablation procedures have relied solely on the subjective skill of the surgeon to determine where and how to perform the ablation. The traditional methods have resulted in high variability in clinical outcomes including from patient to patient, surgeon to surgeon and hospital to hospital.

BRIEF DESCRIPTION OF THE DRAWINGS

A more detailed understanding can be had from the following description, given by way of example in conjunction with the accompanying drawings wherein.

DETAILED DESCRIPTION

Figure 1:
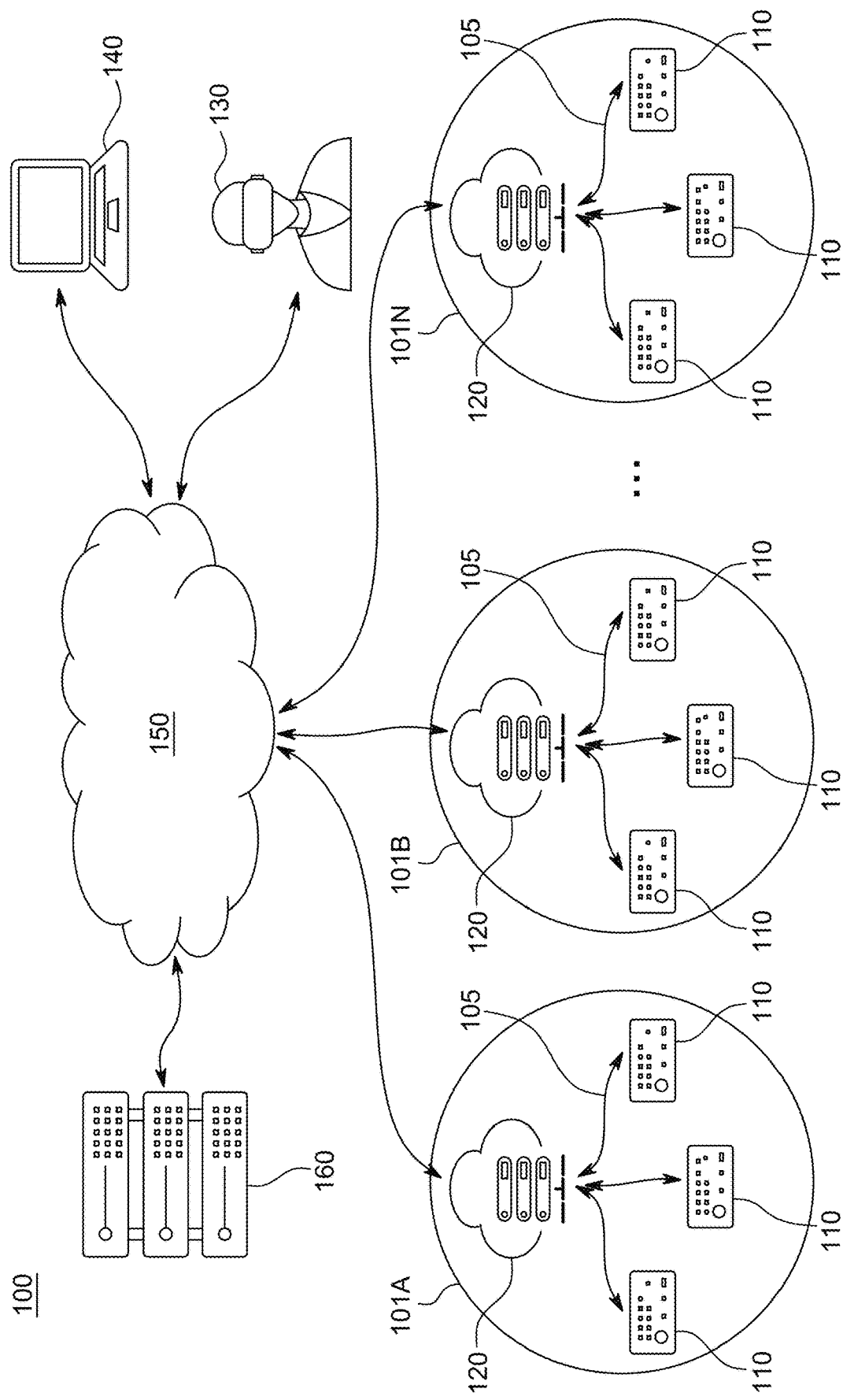
FIG. 1 is a diagram of an example system in which one or more features of the disclosure can be implemented.

The present invention leverages advances in machine learning and big data analytics to improve the clinical techniques of the cardiac ablation procedure. Embodiments of the present invention may use data collected from multiple patients, multiple surgeons and multiple hospitals to generate a cardiac ablation treatment plan. Embodiments of the present invention further improve the clinical outcomes by providing systems and methods that are dynamically adapted while the cardiac ablation procedure is being performed. Embodiments of the present invention may be able to obtain improved clinical outcomes while also maintaining compliance with the United States Health Insurance Portability and Accountability Act of 1996 (HIPAA) and the European Union General Data Protection Regulation (GDPR).

A system and method for improving cardiac ablation procedures are included. The system and method include a cloud server that includes a database containing information about previously performed cardiac ablations, a local server that is communicatively coupled to the cloud server via first network, and a surgical system that is communicatively coupled to the local server via second network, wherein the cloud server is configured to: receive, via the local server, electrical and anatomical data of a heart of a patient from the surgical system, perform a comparison of the electrical and anatomical data of the heart to the database information, generate a surgical treatment plan for the heart based on the comparison, wherein the surgical treatment plan includes a grid of the heart, and transmit, via the local server, the surgical treatment plan to the surgical system. The system and method may include one or more parameters of the surgical system being changed according to the treatment plan. The cloud server may receive the electrical and anatomical data of the heart of the patient from the surgical system while the cardiac ablation procedure is performed. The cloud server may be further configured to: receive additional electrical and anatomical data of the heart after the ablation procedure is performed, and generate an ablation score based on the additional electrical and anatomical data. The ablation procedure may include a plurality of ablations, wherein the cloud server receives the electrical and anatomical data of the heart of the patient from the surgical system after each ablation.

A system and method for training a surgeon to perform a cardiac ablation are included. The system and method include a cloud server that includes a database information about previously performed cardiac ablations, and an AR/VR system that is communicatively coupled to the cloud server via a first network, wherein the AR/VR system is configured to: receive an input of parameters that define a training ablation, receive electrical and anatomical data for a virtual patient from the cloud server, wherein the electrical and anatomical data for a virtual patent are determined by comparing the input to the database information, create a virtual simulation of a heart of the patient based on the electrical and anatomical data for the virtual patient, measure performance of a trainee performing a cardiac ablation procedure on the virtual simulation, and score the performance of the trainee.

FIG. 1 is a diagram of an example system 100 in which one or more features of the disclosure can be implemented. In system 100, a plurality of discrete networks, represented as discrete surgical networks 101A-101N, are connected to a cloud-based platform 160 by public network 150. In some instances, the cloud-based platform 160 is implemented by a public cloud computing platform, such as Amazon Web Services or Microsoft Azure, for example, a hybrid cloud computing platform, such as HP Enterprise OneSphere, for example, or a private cloud computing platform.

The discrete networks 101A-101N may be located within a single physical location, within a single entity network, across physical or entity boundaries, such as at separate hospitals or in separate healthcare provider networks, for example.

In an embodiment, each of the discrete networks 101 includes one or more surgical systems 110 connected to a local server 120. The one or more surgical systems 110 are capable of obtaining anatomical and electrical measurements of a patient's heart and performing a cardiac ablation procedure. An example of a surgical system that may be used in system 100 is the Carto® 3 System sold by Biosense Webster®. In some instances, the surgical system 110 may also associate the measurements with a unique patient identification (ID) or other information that can be used to uniquely identify the patient.

The surgical system 110 may also, and optionally, obtain anatomical measurements of the patient's heart or other measurements related to a patient using ultrasound, computed tomography (CT), magnetic resonance imaging (MRI) or other medical imaging techniques known in the art. The surgical system 110 may obtain electrical measurements using catheters, electrocardiograms (EKGs) or other sensors that measure electrical properties of the heart. The anatomical and electrical measurements may then be stored in a local memory of the surgical system 110 and transmitted to the local server 120 using the private network 105. In some instances, the electrical and anatomical measurements are transmitted to local server 120 immediately on acquisition.

The surgical system 110 then generates mappings of the patient's heart by combining the electrical and anatomical measurements. The mappings of the patient's heart may be stored in the local memory of the surgical system 110 and transmitted to the local server 120 using the private network 105. In some instances, the mappings and/or the measurements may be transmitted to local server 120 immediately upon generation.

In one embodiment, the surgical system 110 enables a surgeon to perform a cardiac ablation procedure. In some instances, the cardiac ablation procedure may utilize contact force technology and irrigated ablation technology. During the cardiac ablation procedure, the surgical system 110 acquires and stores information regarding the patient's heart and the ablation procedure. For example, the stored information may include arrhythmias, procedure duration, catheters used, ablation session count and location, mapping duration, ablation duration, ablation power and other measurable parameters and settings that are typically gathered, or optional parameters or settings that may be gathered, about the particular cardiac ablation. In addition, the information about the ablation procedure may also include information regarding the physician that performed the procedure, the particular surgical theater where the procedure was performed as well information to identify any support staff that assisted in the procedure. The surgical system 110 may save the information about the ablation procedure in the local memory and may transmit the information to the local server 120 using the private network 105. In some instances, the information about the ablation procedure is transmitted to local server 120 during the procedure, and in other instances, the information may be transmitted at the completion of the ablation procedure.

Private network 105 may be any network or system generally known in the art such as an intranet, a local area network (LAN), a wide area network (WAN), a metropolitan area network (MAN), a direct connection or series of connections, a cellular telephone network, or any other network or medium capable of facilitating communication between the surgical systems 110 and the local server 120. The private network 105 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the private network 105.

The local server 120 receives the electrical and anatomical measurements, the mappings and the information regarding the ablation procedure in a local database. In some instances, the local database associates the data received with unique patient identifiable information. In these instances, the local server 120 may save this "individually identifiable health information." in compliance with the Health Insurance Portability and Accountability Act of 1996 (HIPAA).

Additionally, or alternatively, data anonymization or data synthesis may be used. The data anonymization or data synthesis is a process by which new data is generated, be it based on original real data, a real data schema, or via the use of random generation to provide synthetic data. Synthetic data may be configured to have greater or lesser analytical utility when compared with the original dataset. Synthetic data can also be configured to have greater or lesser privacy, re-identification, or disclosure risk when compared with the original dataset. In one embodiment, synthetic data may be based on a single patent's data which has been modified slightly in a random manner. In another embodiment, synthetic data may be data from multiple patients, specifically selected (from a specific data set, a specific physician, a specific hospital or a specific condition) or randomly selected, which has been averaged to create a synthetic data set. It would be understood by those of skill in the art that there are many ways in which a synthetic data set may be generated within the scope of the present teachings. In general, a tradeoff exists between analytical utility and privacy risk for any data synthesis technique. Synthetic data may be used in cases when real data is either not available or is less than desirable or feasible to use.

In some instances, the local server 120 is implemented as a physical server. In other instances, the local server 120 is implemented as a virtual server such as via public cloud computing provider (e.g., Amazon Web Services® (AWS).

In some instances, the local server 120 uses machine learning or other artificial intelligence techniques to analyze the data stored in the local database. The local server may use the machine learning to: 1) consider all of the prior patients having similar cardiac conditions and morphologies and the associated ablation procedure data and best outcomes from prior patients in order to recommend optimal treatment plans for a cardiac ablation to be performed; 2) modify a treatment plan while the cardiac ablation is being performed and make specific recommendations to a physician during the ablation procedure, considering the aforementioned prior patient and ablation data; and/or 3) to evaluate the performance of the surgeon that performed the cardiac ablation in view of the treatment plan and the outcome of the patient. In this manner, a physician has the accumulated experience of all prior patients and cardiac procedures at their disposal in planning, treating and evaluating an ablation procedure in order to achieve the best patient outcomes.

In an alternative embodiment, the local server may anonymize the electrical and anatomical measurements, the mappings and the information regarding the ablation procedure to form anonymized data. The local server 120 may then be able to transmit the anonymized data to the cloud-based platform 160 via the public network 150 without any risk of falling out of compliance with HIPPA or GDPR regulations. Using the anonymized data greatly expands the experience database available to physicians on the public network 150. One of sill in the art would understand that there are many standard techniques for anonymizing data, and a detailed description of such a procedure is outside the scope of the present description.

Collection and analysis of data regarding a specific procedure may include statistics on the procedure are available by respective patients, broken down by specific and separate portions of the procedure. This may help physicians and researchers measure the effect of any parameter over any other parameter. In one example, collection and analysis of such data enables researchers to evaluate any changes that are introduced into the cardiac catheter procedure, for example, a new catheter, a new version of the Carto® software or the like. This may allow researchers to determine if these changes improve patient outcomes.

Public network 150 may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between the discrete networks 101A-101N and the cloud-based platform 160. The public network 150 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the public network 150.

The cloud-based platform 160 receives the anonymized data from each local server 120 of the discrete networks 101A-101N and stores the received information in an anonymized database. In some instances, the local server 120 uses machine learning or other artificial intelligence techniques to analyze the data stored in the local database. The local server may use the machine learning to: 1) consider all of the prior patents having similar cardiac conditions and morphologies and the associated ablation procedure data and best outcomes from prior patients in order to recommend optimal treatment plans for a cardiac ablation to be performed; 2) modify a treatment plan while the cardiac ablation is being performed and make specific recommendations to a physician during the ablation procedure, considering the aforementioned prior patient and ablation data; and/or 3) to evaluate the performance of the surgeon that performed the cardiac ablation in view of the treatment plan and the outcome of the patient. In this manner, a physician has the accumulated experience of all prior patients and cardiac procedures at their disposal in planning, treating and evaluating an ablation procedure in order to achieve the best patient outcomes.

In many instances, the cloud-based platform 160 also provides a portal for $3^{rd}$ parties 140 to query the data stored in the anonymized database via the public network 150. In some instances, the $3^{rd}$ party 140 may use a standard internet browser to access the portal of the cloud-based platform 160. In other instances, a dedicated application is required for the $3^{rd}$ party 140 to access the portal of the cloud-based platform 160.

The cloud-based platform may also provide access to the information in an anonymized database to an augmented reality (AR)/virtual reality (VR) system 130. The AR/VR system 130 enables a surgeon to train to perform cardiac ablation procedures based on the data collected on actual cardiac ablations.

AR/VR system 130 enables a user to provide training of interest. While a standard display presents an entire view of the system, the AR/VR system 130 enables providing an algorithm, as will be described, to areas where there is an interest in collecting more information. The AR/VR system 130 enables a focus to be placed upon specific diagnostic elements, such as routing the ultrasound catheter beam to a certain area, and/or defining the mapping system to modify the resolution of the maps in an area of interest, such as a point density of 1 mm to 0.5 mm or even to 0.1 mm, to enable viewing of the area.

Figure 2A:
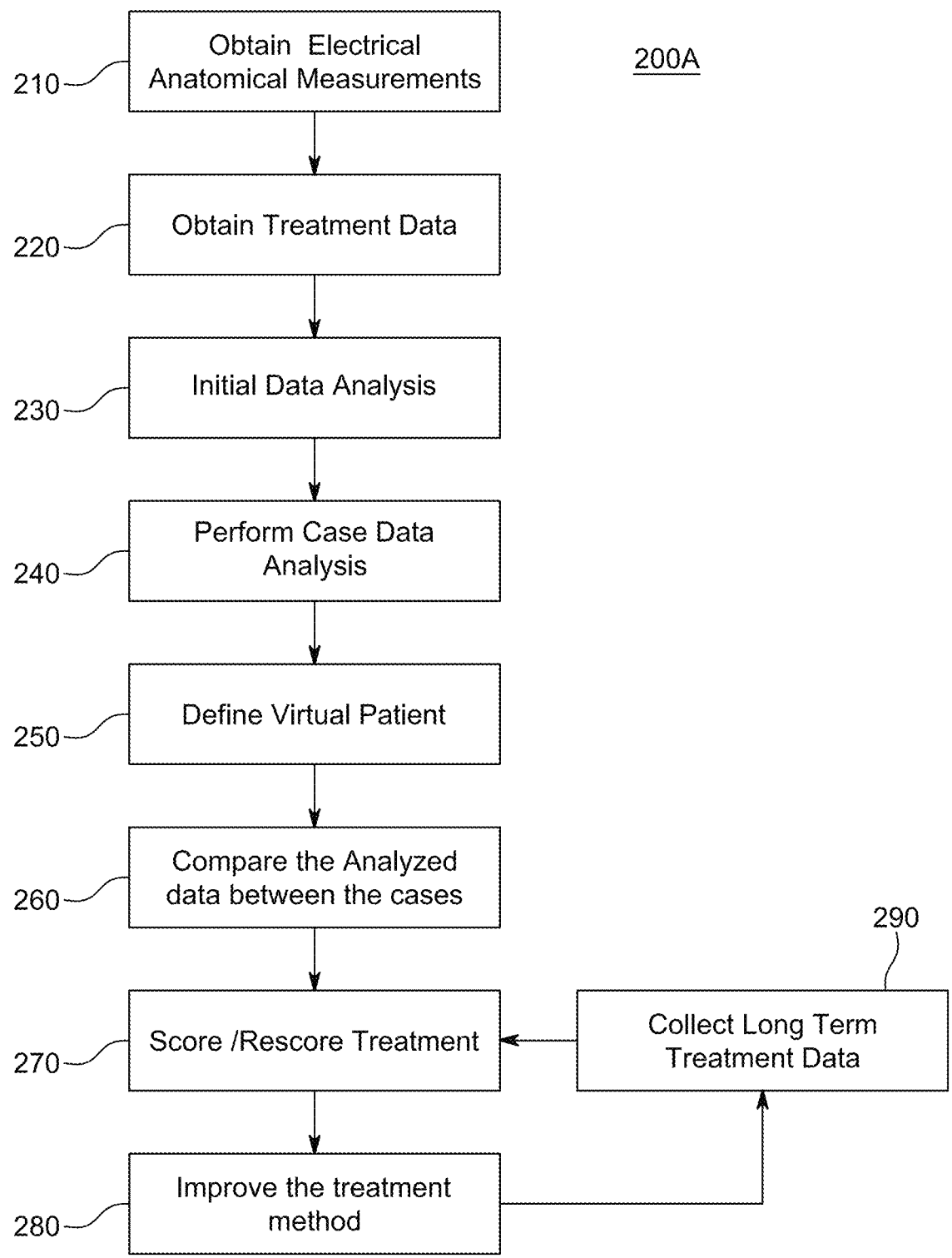
FIG. 2A illustrates a process of performing an analysis of cardiac ablation data.

FIG. 2A illustrates a process 200A of collecting the data and performing an analysis that provides for better future treatments using retrospective analysis. At step 210, electrical measurements and anatomical measurements of the patient's heart are recorded using the surgical system 110 prior to the patient receiving the cardiac ablation treatment. The available treatment data collected during the cardiac ablation procedure is recorded by the surgical system at step 220.

At step 230, an initial data analysis is performed based on the electrical and measurements and anatomical measurements recorded during step 210 and the treatment data collected during step 230. The initial data analysis may identify the procedure parameters, this includes information that can be used for identifying "Similar Patients" based on clinical parameters and identifying the treatment method characteristics, e.g., how much ablation energy was supplied in what distance, based on electro anatomical parameters.

At step 240, additional information about the patient may be obtained. For example, patient medical history and patient continuum care, such as from EMR, from patient feedback and from a heart monitoring device, for example, received manually, such as by filling forms, or via connectivity to other systems.

At step 250, additional analysis is performed based on the collected information from step 230, step 220, and step 210 to define "virtual patient" characteristics, treatment approach, and "expected outcome." Groups of similar "virtual patients" are identified at step 260. The groups of similar "virtual patients" are identified at step 260 by comparing the "virtual patient" defined at step 250 with previously defined virtual patients.

The treatments are scored, at step 270, based on available long term clinical outcomes, including short-term, medium-term and long-term outcome timeframes. At step 280, the recommended treatment for groups of similar "virtual patients" based on the scores calculated at step 270. Additional long-term treatment data is then collected about the patients at step 290. The long-term treatment data may include a beginning score, the results based on 1 year continuum case data and after rescoring based on 3 years continuum case data. This additional data when collected is then used by step 270 to update the treatment scores.

Figure 2B:
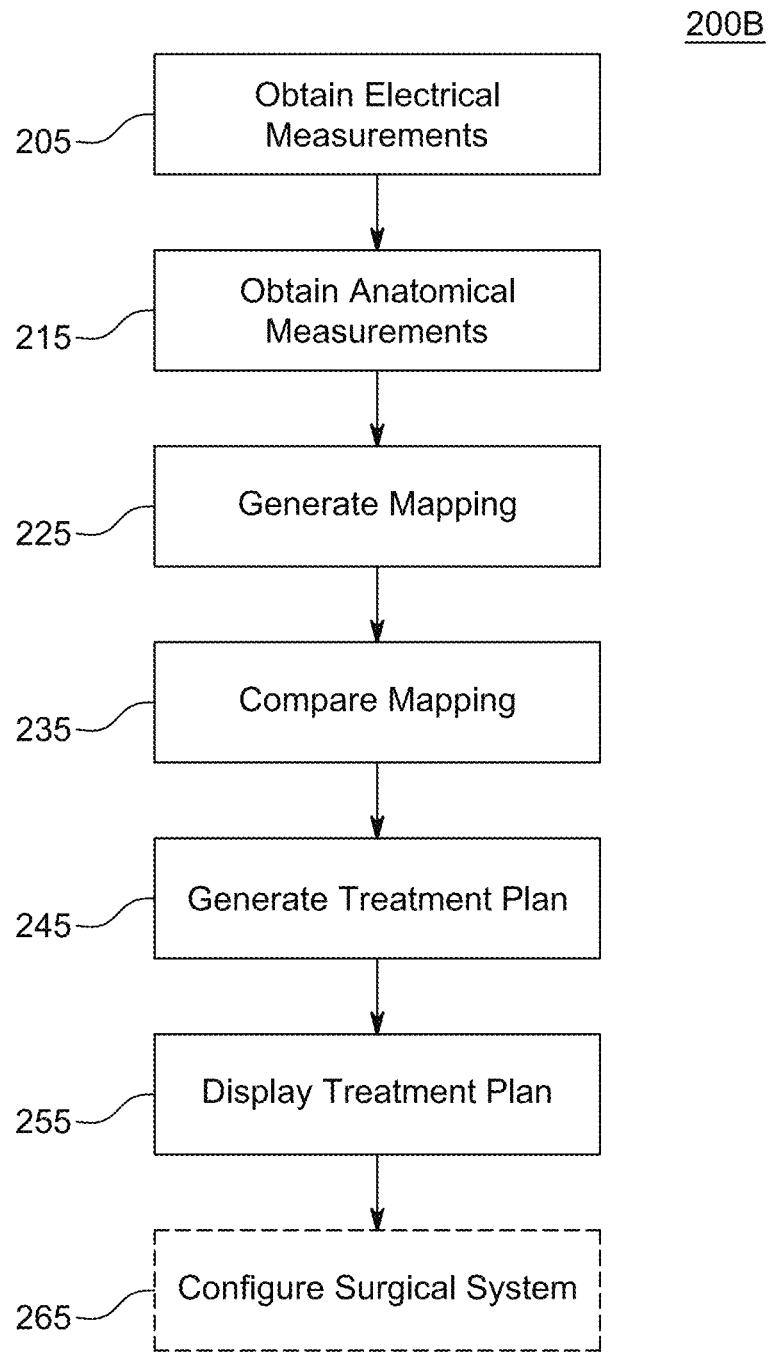
FIG. 2B illustrates a process for generating a cardiac ablation treatment plan according to certain embodiments.

FIG. 2B illustrates a process 200B for generating a cardiac ablation treatment plan according to certain embodiments. At step 205, the electrical measurements of the patient's heart are obtained by surgical system 110. At step 220, surgical system 110 acquires the anatomical measurements of the patients. Based on the electrical measurements and the anatomical measurements acquired at step 205 and step 220, surgical system 110 generates mappings of the patient's heart at step 225.

At step 235, the mapping of the patient's heart, the anatomical measurements and electrical measurements of the patient's heart are compared to data collected in previous cardiac ablation procedures. Such different types of data is noted in detail hereinafter. Differences and correlations are determined, and a treatment plan for the cardiac ablation procedure is then generated at step 245 and displayed by the surgical system 110 at step 255.

Optionally, at step 265, parameters of the surgical system 110 are automatically configured to perform the cardiac ablation according to the treatment plan generated at step 245. The parameters of the surgical system 110 that may be configured include the intensity, duration, number, and location of the ablations. If the ablation is to be performed by a physician, the physician utilizes the treatment plan as a guide for the procedure. Alternatively, if the ablation is to be assisted or performed, in whole or in part, by surgical robotics, the treatment plan may be the roadmap for the automated surgical robotics system; i.e., the location and duration of each ablation is input into the automated surgical robots system, and the treatment plan is carried out. Such a surgical system is the Monarch surgical robotics system by Auris Health, Inc. of Redwood City, Calif.

In some instances, step 235 and step 245 may be performed by the surgical system 110 transmitting the mapping of the patient's heart, the anatomical measurements and electrical measurements of the patient's heart to the local server 120. The local server 120 may utilize machine learning to compare the information received from the surgical system to the data stored in the local database. The local server 120 then transmits the results of the comparison back to the surgical system 110 via the private network 105.

In other instances, step 235 and step 245 may be performed by the surgical system 110 transmitting the mapping of the patient's heart, the anatomical measurements and electrical measurements of the patient's heart to the cloud-based platform 160 via the local server 120. The local server 120 removes any "individually identifiable health information" before transmitting the information to the cloud platform 160. The cloud-based platform 160 then utilizes machine learning to compare the information received from the surgical system to the data stored in the anonymized database. The cloud-based platform 160 transmits the results of the comparison back to the surgical system 110 via the public network 150 and the local server 120.

During the procedure, the system may collect a multitude of information regarding the procedure, which may be broken down and later analyzed by the physician during an evaluation phase.

Figure 3:
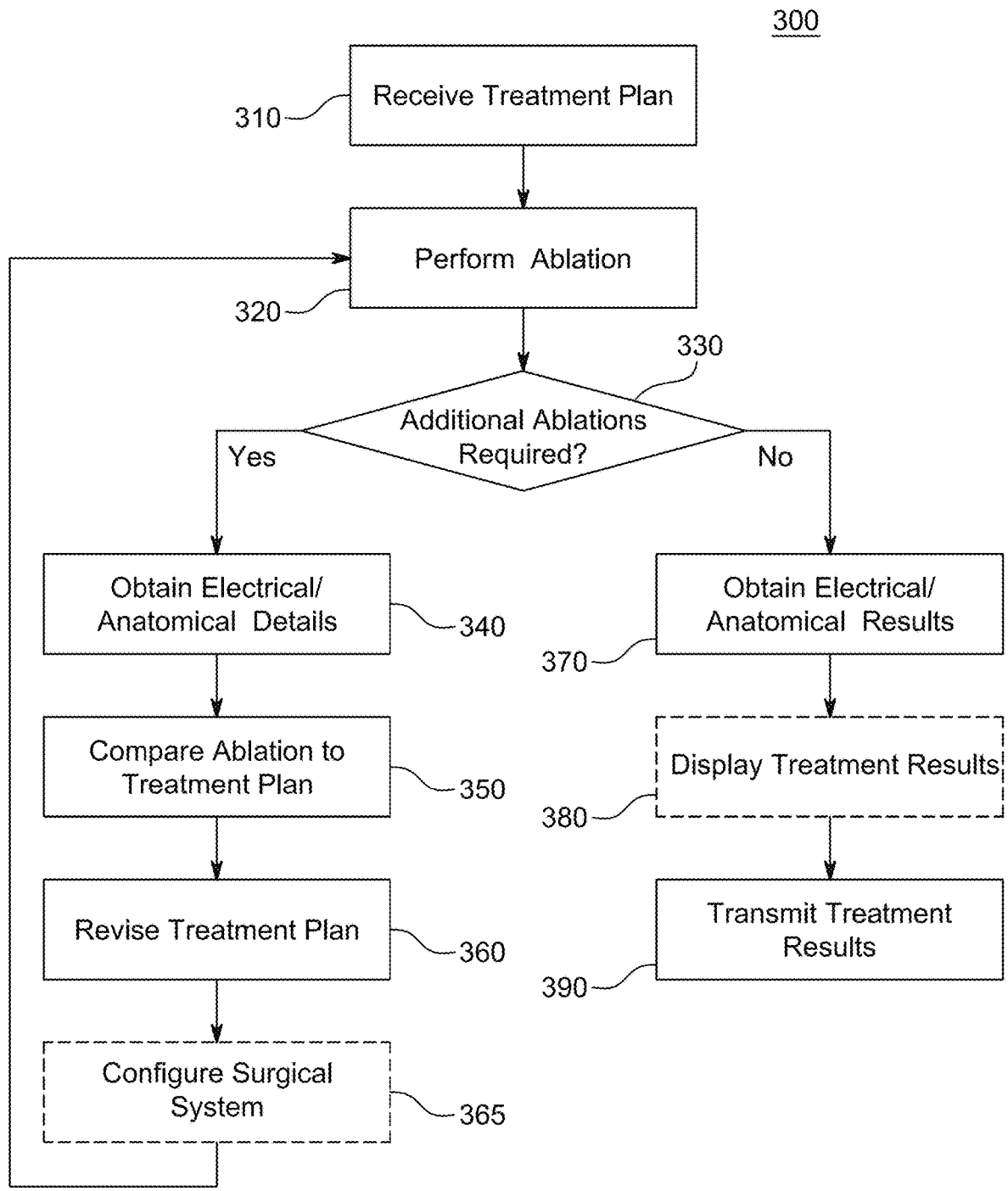
FIG. 3 illustrates a process for performing a cardiac ablation treatment according to certain embodiments.

FIG. 3 illustrates a process 300 for performing a cardiac ablation treatment according to certain embodiments. At step 310, the cardiac ablation treatment plan is received by the surgical system 110. In many instances, the cardiac ablation treatment plan is generated using process 200. At step 320, the surgeon uses the surgical system 110 to perform the cardiac ablation according to the treatment plan. At step 330, the surgical system 110 determines if additional ablations are required based on the treatment plan.

If no addition ablations are required, surgical system 110 obtains post-ablation electrical and anatomical measurements of the patient's heart at step 370. Optionally, at step 370, the post-ablation electrical and anatomical measurements are displayed by the surgical system 110. At step 390, the post-ablation electrical and anatomical measurements and the information about the ablation procedure are transmitted to the local server 120 via the private network 105.

If additional ablations are required, surgical system 110 obtains additional electrical and anatomical measurements of the patient's heart at step 340. Then at step 350, the additional electrical and anatomical measurements are compared with the treatment plan. Based on the comparison, the treatment plan is revised at step 360. The revision to the treatment plan may be required because of errors or inaccuracies in the particular ablation performed at step 320 or variations in the patient's physiology. Optionally, at step 365, the parameters of the surgical system 110 may be automatically configured to perform the cardiac ablation according to the revised treatment plan generated at step 360. The parameters of the surgical system include the intensity, duration, number, and location of the ablations. The surgeon may perform the additional ablations according to the revised treatment plan at step 320. In such a manner, the system may suggest improvements or alternatives to the physician "live" allowing the physician multiple options for treatment if unexpected difficulties arise during the procedure. The system may evaluate each portion of the procedure, and provide constant feedback to the physician. For example, if the treatment plan required an ablation at a position X, and the physician deviated from that plan, even slightly, a modified ablation scheme from the deviation may then be necessary.

In one alternative embodiment, the system may provide a detailed "grid" on the heart, thereby allowing the physician to be guided to a specific spot with a high degree of accuracy. An example gird is shown in FIG. 6B discussed herein below. Such a grid may allow for easier comparison and analysis of mappings of hearts across patients to allow for suggestions for local activation time (LAT) mapping, cycle length (CL) mapping and ripple frequency, and combining to determine the success of the treatment plans are doing. It should be noted that the grid as shown is greatly simplified for explanation, and a grid that is utilized for actual ablations would likely have much greater granularity and thus greater resolution. However, the same concepts apply regardless of the granularity of the mapping.

Additionally, the system allows for follow up information to be recorded and considered via, for example, a halter/recorder, for longer-term data allowing processes and procedures to be correlated with positive patient outcomes.

The system also permits the inclusion of patient "forms" in order to collect additional information regarding a patient that may not be specifically related to the patient's cardio physiology. Form function and information may include, e.g. medical history forms to determine a patient's age, weight, medications, etc. These forms may allow the collection of, and recommendation of, a continuum of care information for the short-term, 12 weeks for example, the medium-term, 1 year for example, and/or the long-term, 3-5 years or more for example.

Utilizing such data and AI/machine learning algorithms, the system can develop predictive algorithms based on different "categories" of people, conditions, and the like. In some instances, step 340 and step 350 are performed by surgical system 110 transmitting the additional electrical and anatomical measurements to the local server 120. The local server 120 may utilizes machine learning to compare the information received from the surgical system to the data stored in the local database. The local server 120 then transmits the results of the comparison back to the surgical system 110 via the private network 105.

In other instances, step 340 and step 350 are performed by the surgical system 110 transmitting the additional electrical and anatomical measurements to the cloud-based platform 160 via the local server 120. In this instance, the local server 120 removes any "individually identifiable health information" before transmitting the information to the cloud platform 160. The cloud-based platform 160 may utilize machine learning to compare the information received from the surgical system to the data stored in the anonymized database. The cloud-based platform 160 then transmits the results of the comparison back to the surgical system 110 via the public network 150 and the local server 120.

Figure 4:
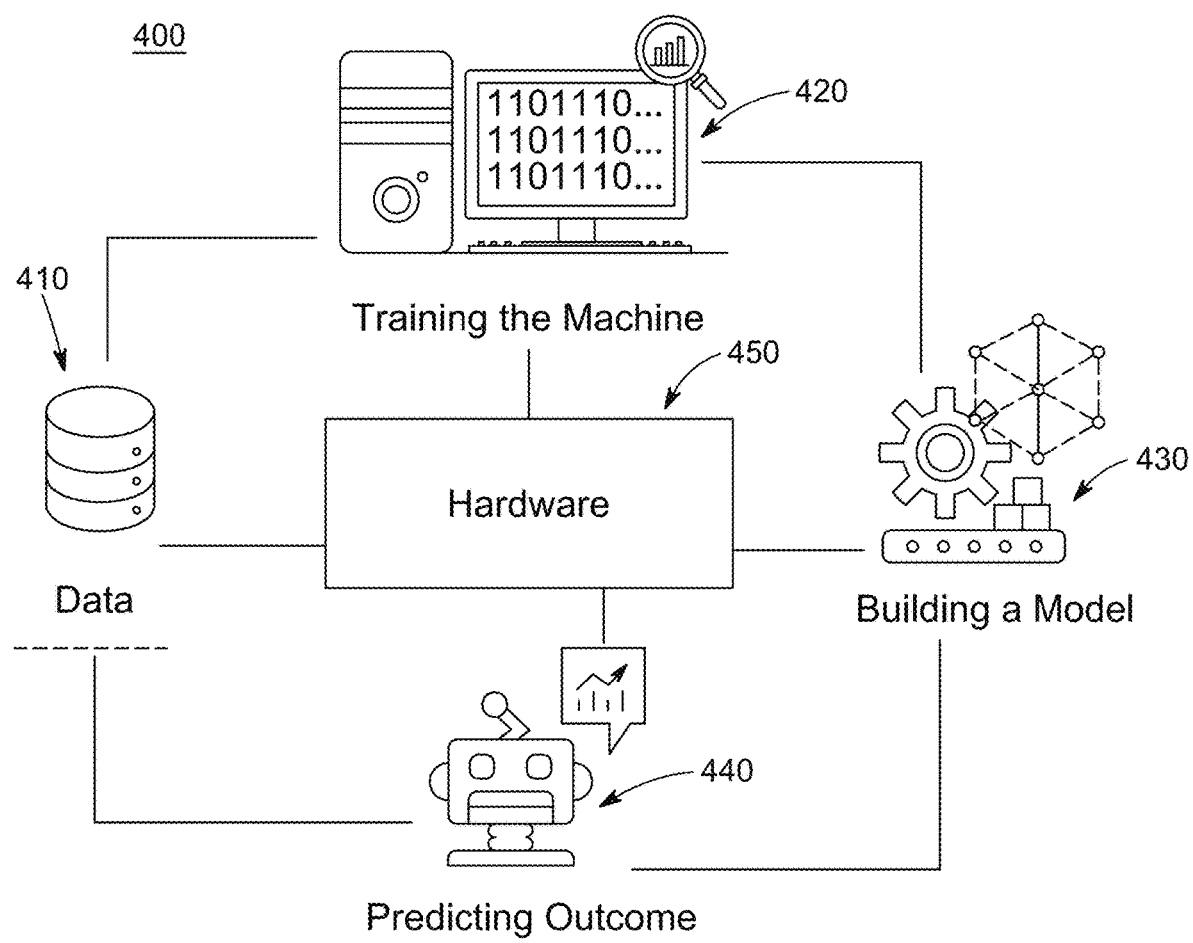
FIG. 4 illustrates a graphical depiction of an artificial intelligence system.

FIG. 4 illustrates a graphical depiction of an artificial intelligence system 400 according to the embodiments disclosed herein. System 400 includes data 410, a machine 420, a model 430, a plurality of outcomes 440 and underlying hardware 450. System 400 operates by using the data 410 to train the machine 420 while building a model 430 to enable a plurality of outcomes 440 to be predicted. The system 400 may operate with respect to hardware 450. In such a configuration, the data 410 may be related to hardware 450 and may originate with surgical system 110, for example. For example, the data 410 may be on-going data, or output data associated with hardware 450. The machine 420 may operate as the controller or data collector associated with the hardware 450, or be associated therewith. The model 430 may be configured to model the operation of hardware 450 and model the data 410 collected from hardware 450 in order to predict the outcome achieved by hardware 450. Using the outcome 440 that is predicted, hardware 450 may be configured to provide a certain desired outcome 440 from hardware 450.

Figure 5:
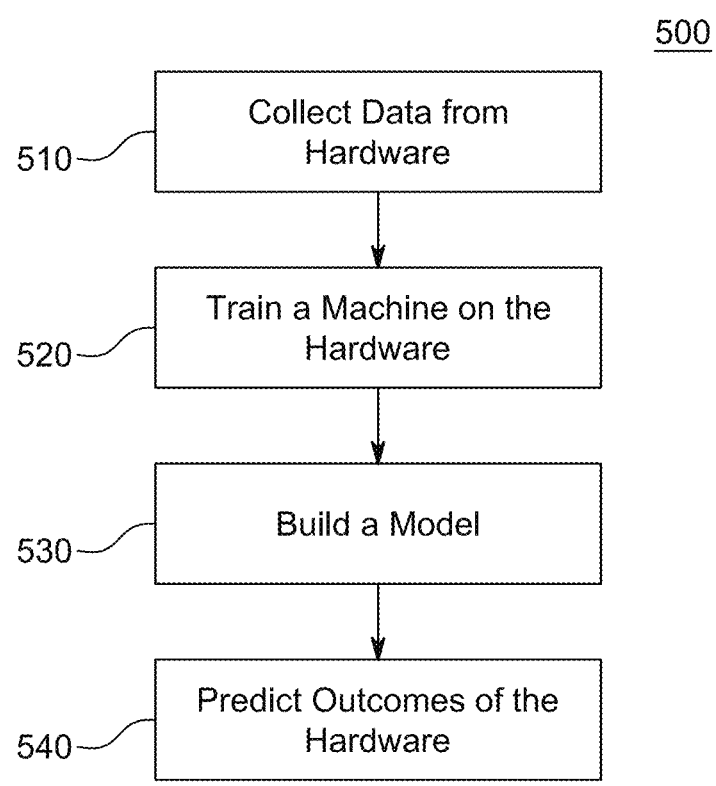
FIG. 5 illustrates a method performed in the artificial intelligence system of FIG. 4.

FIG. 5 illustrates a method 500 performed in the artificial intelligence system of FIG. 4. Method 500 includes collecting data from the hardware at step 510. This data may include currently collected, historical or other data from the hardware. For example, this data may include measurements during a surgical procedure and may be associated with the outcome of the procedure. For example, the temperature of a heart may be collected and correlated with the outcome of a heart procedure.

At step 520, method 500 includes training a machine on the hardware. The training may include an analysis and correlation of the data collected in step 510. For example in the case of the heart, the data of temperature and outcome may be trained to determine if a correlation or link exists between the temperature of the heart during the procedure and the outcome.

At step 530, method 500 includes building a model on the data associated with the hardware. Building a model may include physical hardware or software modeling, algorithmic modeling and the like, as will be described below. This modeling may seek to represent the data that has been collected and trained.

At step 540, method 500 includes predicting the outcomes of the model associated with the hardware. This prediction of the outcome may be based on the trained model. For example, in the case of the heart, if the temperature during the procedure between 97.7-100.2 produces a positive result from the procedure, the outcome can be predicted in a given procedure based on the temperature of the heart during the procedure. While this model is rudimentary, it is provided for exemplary purposes and to increase understanding of the present invention.

The present system and method operate to train the machine, build the model and predict outcomes using algorithms. These algorithms may be used to solve the trained model and predict outcomes associated with the hardware. These algorithms may be divided generally into classification, regression and clustering algorithms.

For example, a classification algorithm is used in the situation where the dependent variable, which is the variable being predicted, is divided into classes and predicting a class, the dependent variable, for a given input. Thus, a classification algorithm is used to predict an outcome, from a set number of fixed, predefined outcomes. A classification algorithm may include naive Bayes algorithms, decision trees, random forest classifiers, logistic regressions, support vector machines and k nearest neighbors.

Generally, a naive Bayes algorithm follows the Bayes theorem, and follows a probabilistic approach. As would be understood, other probabilistic-based algorithms may also be used, and generally operate using similar probabilistic principles to those described below for the exemplary naive Bayes algorithm.

Figure 6:
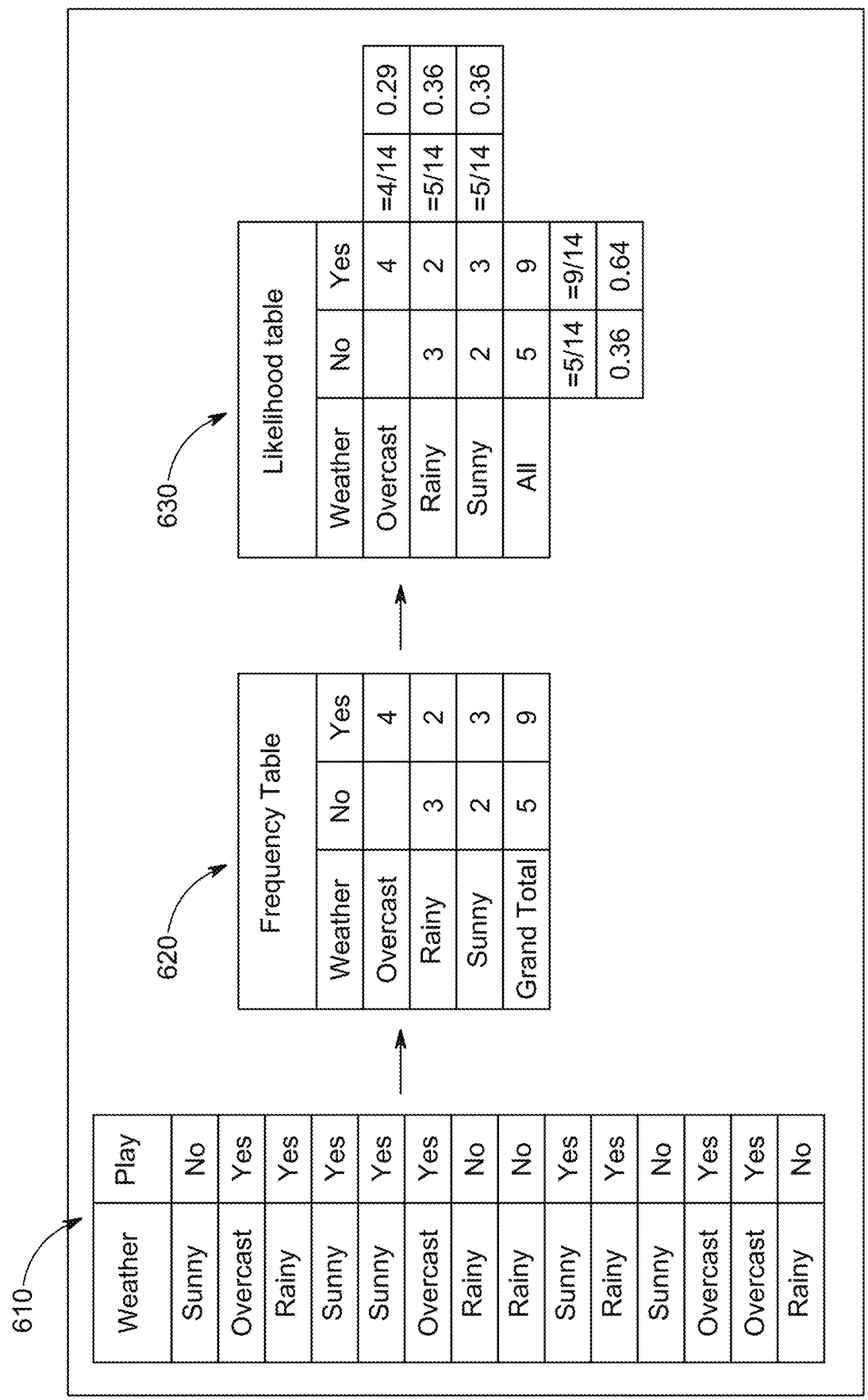
FIG. 6 illustrates an example of the probabilities of a naive Bayes calculation.

FIG. 6 illustrates an example of the probabilities of a naive Bayes calculation. The probability approach of Bayes theorem essentially means that instead of jumping straight into the data, the algorithm has a set of prior probabilities for each of the classes for the target. After the data is entered, the naive Bayes algorithm may update the prior probabilities to form a posterior probability. This is given by the formula:

$$\text{posterior} = \frac{\text{prior} \times \text{likelihood}}{\text{evidence}}$$

This naive Bayes algorithm, and Bayes algorithms generally, may be useful when needing to predict whether your input belongs to a given list of n classes or not. The probabilistic approach may be used because the probabilities for all the n classes will be quite low.

For example, as illustrated in FIG. 6, a person playing golf, which depends on factors including the weather outside shown in a first data set 610. The first data set 610 illustrates the weather in a first column and an outcome of playing associated with that weather in a second column. In the frequency table 620 the frequencies with which certain events occur are generated. In frequency table 620, the frequency of a person playing or not playing golf in each of the weather conditions is determined. From there, a likelihood table is compiled to generate initial probabilities. For example, the probability of the weather being overcast is 0.29 while the general probability of playing is 0.64.

The posterior probabilities may be generated from the likelihood table 630. These posterior probabilities may be configured to answer questions about weather conditions and whether golf is played in those weather conditions. For example, the probability of it being sunny outside and golf being played may be set forth by the Bayesian formula:

$P(\text{Yes}|\text{Sunny}) = P(\text{Sunny}|\text{Yes}) * P(\text{Yes}) / P(\text{Sunny})$ According to likelihood table 630:

$P(\text{Sunny}|\text{Yes}) = 3/9 = 0.33$, $P(\text{Sunny}) = 5/14 = 0.36$, $P(\text{Yes}) = 9/14 = 0.64$.

Therefore the P(Yes|Sunny)=0.33*0.64/0.36 or approximately 0.60 (60%).

Generally, a decision tree is a flowchart-like tree structure where each external node denotes a test on an attribute and each branch represents the outcome of that test. The leaf nodes contain the actual predicted labels. The decision tree begins from the root of the tree with attribute values being compared until a leaf node is reached. A decision tree can be used as a classifier when handling high dimensional data and when little time has been spent behind data preparation. Decision trees may take the form of a simple decision tree, a linear decision tree, an algebraic decision tree, a deterministic decision tree, a randomized decision tree, a nondeterministic decision tree, and a quantum decision tree. An exemplary decision tree is provided below in FIG. 7.

Figure 7:
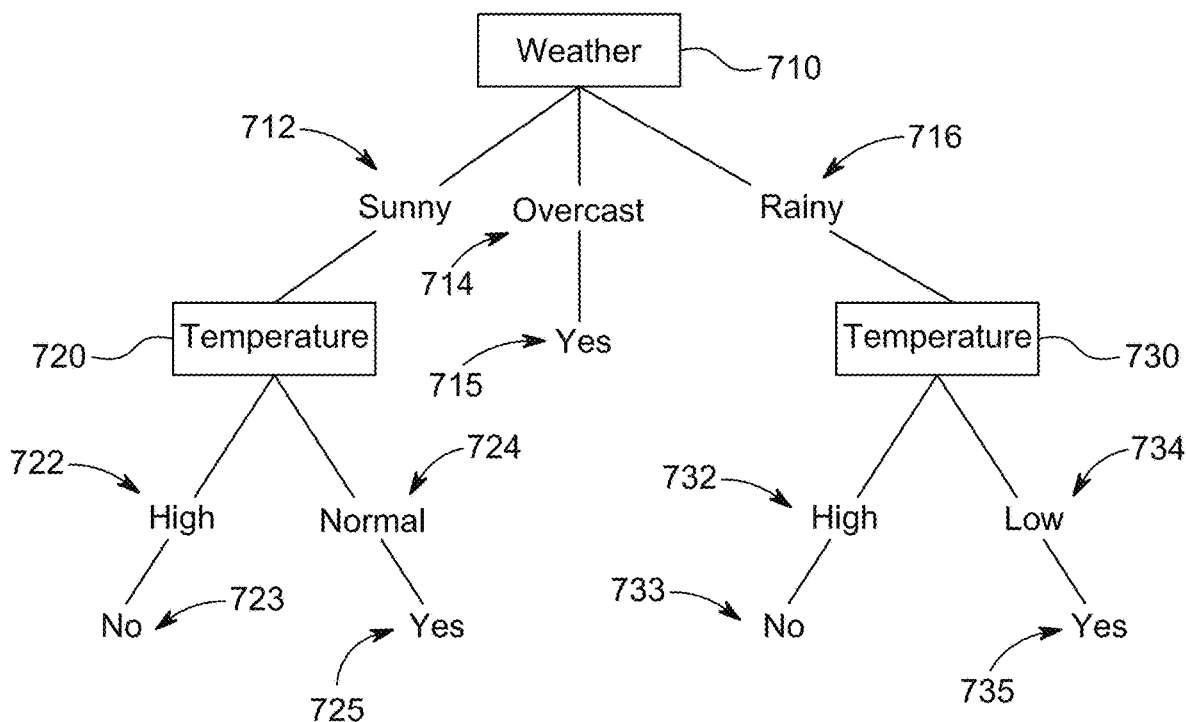
FIG. 7 illustrates an exemplary decision tree.

FIG. 7 illustrates a decision tree, along the same structure as the Bayes example above, in deciding whether to play golf. In the decision tree, the first node 710 examines the weather providing sunny 712, overcast 714, and rain 716 as the choices to progress down the decision tree. If the weather is sunny, the leg of the tree is followed to a second node 720 examining the temperature. The temperature at node 720 may be high 722 or normal 724, in this example. If the temperature at node 720 is high 722, then the predicted outcome of "No" 723 golf occurs. If the temperature at node 720 is normal 724, then the predicted outcome of "Yes" 725 golf occurs.

Further, from the first node 710, an outcome overcast 714, "Yes" 715 golf occurs.

From the first node weather 710, an outcome of rain 716 results in the third node 730 (again) examining temperature. If the temperature at third node 730 is normal 732, then "Yes" 733 golf is played. If the temperature at third node 730 is low 734, then "No" 735 golf is played.

From this decision tree, a golfer plays golf if the weather is overcast 715, in normal temperature sunny weather 725, and in normal temperature rainy weather 733, while the golfer does not play if there are sunny high temperatures 723 or low rainy temperatures 735.

A random forest classifier is a committee of decision trees, where each decision tree has been fed a subset of the attributes of data and predicts on the basis of that subset. The mode of the actual predicted values of the decision trees are taken into account to provide an ultimate random forest answer. The random forest classifier, generally, alleviates overfitting, which is present in a standalone decision tree, leading to a much more robust and accurate classifier.

Figure 8:
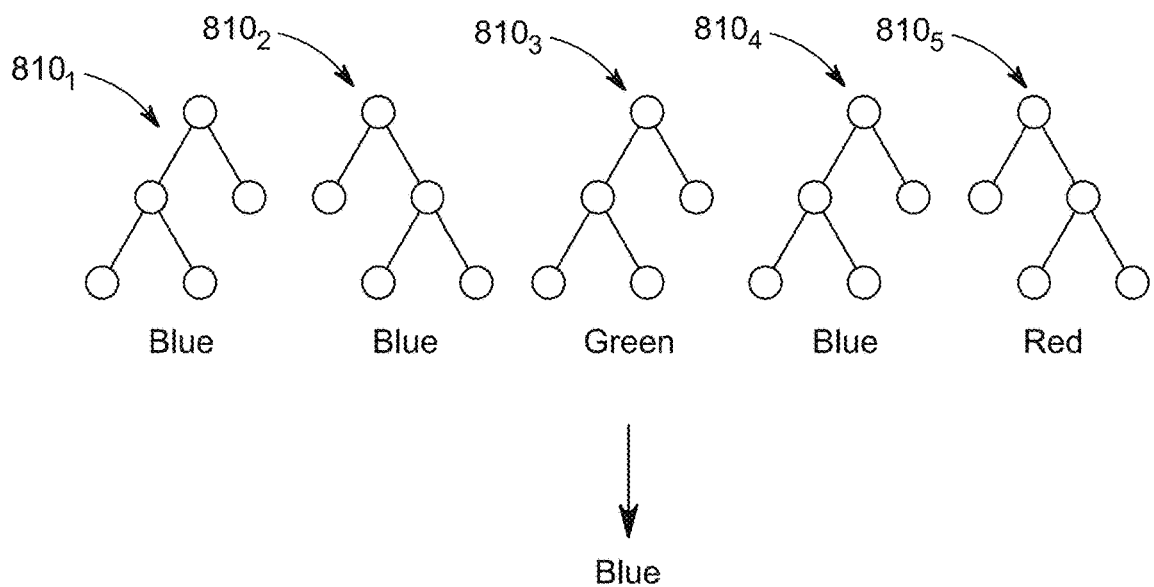
FIG. 8 illustrates an exemplary random forest classifier.

FIG. 8 illustrates an exemplary random forest classifier for classifying the color of a garment. As illustrated in FIG. 8, the random forest classifier includes five decision trees $810_1$, $810_2$, $810_3$, $810_4$, and $810_5$ (collectively or generally referred to as decision trees 810). Each of the trees is designed to classify the color of the garment. A discussion of each of the trees and decisions made is not provided, as each individual tree generally operates as the decision tree of FIG. 7. In the illustration, three ($810_1$, $810_2$, $810_4$) of the five trees determine that the garment is blue, while one determines the garment is green ($810_3$) and the remaining tree determines the garment is red ($810_5$). The random forest takes these actual predicted values of the five trees and calculates the mode of the actual predicted values to provide random forest answer that the garment is blue.

Logistic Regression is another algorithm for binary classification tasks. Logistic regression is based on the logistic function, also called the sigmoid function. This S-shaped curve can take any real-valued number and map it between 0 and 1 asymptotically approaching those limits. The logistic model may be used to model the probability of a certain class or event existing such as pass/fail, win/lose, alive/dead or healthy/sick. This can be extended to model several classes of events such as determining whether an image contains a cat, dog, lion, etc. Each object being detected in the image would be assigned a probability between 0 and 1 with the sum of the probabilities adding to one.

In the logistic model, the log-odds (the logarithm of the odds) for the value labeled "1" is a linear combination of one or more independent variables ("predictors"); the independent variables can each be a binary variable (two classes, coded by an indicator variable) or a continuous variable (any real value). The corresponding probability of the value labeled "1" can vary between 0 (certainly the value "0") and 1 (certainly the value "1"), hence the labeling; the function that converts log-odds to probability is the logistic function, hence the name. The unit of measurement for the log-odds scale is called a logit, from logistic unit, hence the alternative names. Analogous models with a different sigmoid function instead of the logistic function can also be used, such as the probit model; the defining characteristic of the logistic model is that increasing one of the independent variables multiplicatively scales the odds of the given outcome at a constant rate, with each independent variable having its own parameter; for a binary dependent variable this generalizes the odds ratio.

In a binary logistic regression model, the dependent variable has two levels (categorical). Outputs with more than two values are modeled by multinomial logistic regression and, if the multiple categories are ordered, by ordinal logistic regression (for example the proportional odds ordinal logistic model). The logistic regression model itself simply models probability of output in terms of input and does not perform statistical classification (it is not a classifier), though it can be used to make a classifier, for instance by choosing a cutoff value and classifying inputs with probability greater than the cutoff as one class, below the cutoff as the other; this is a common way to make a binary classifier.

Figure 9:
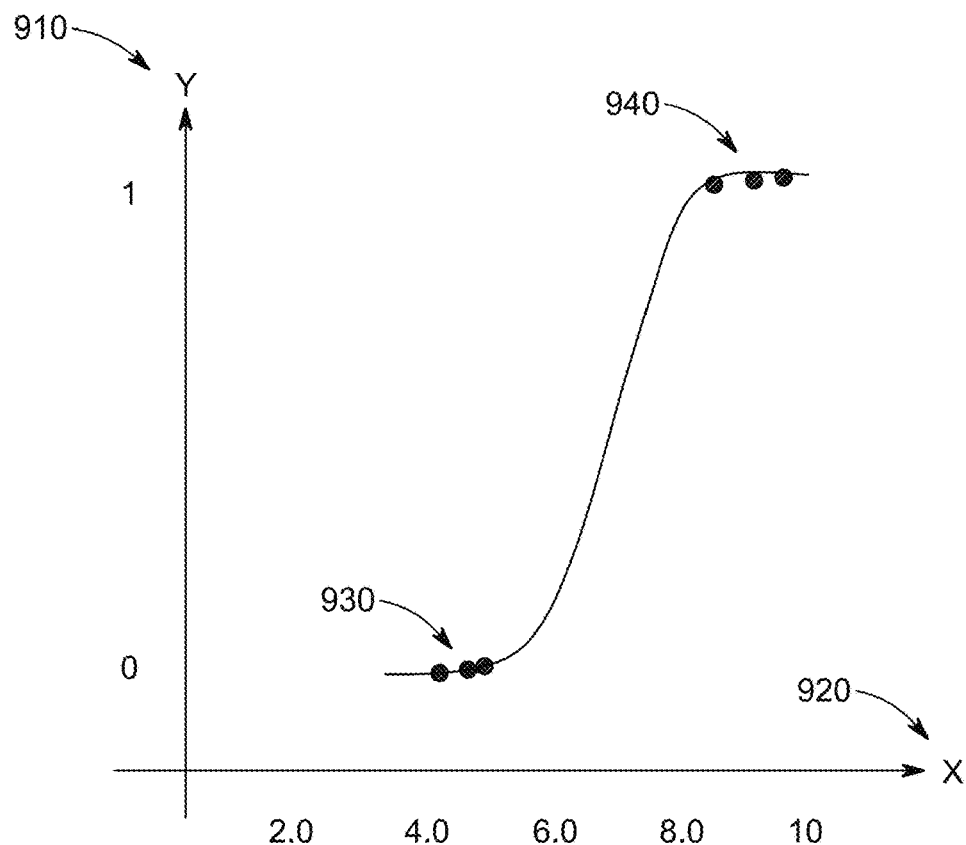
FIG. 9 illustrates an exemplary logistic regression.

FIG. 9 illustrates an exemplary logistic regression. This exemplary logistic regression enables the prediction of an outcome based on a set of variables. For example, based on a person's grade point average and outcome of being accepted to a school may be predicted. The past history of grade point averages and the relationship with acceptance enables the prediction to occur. The logistic regression of FIG. 9 enables the analysis of the grade point average variable 920 to predict the outcome 910 defined by 0 to 1. At the low end 930 of the S-shaped curve, the grade point average 920 predicts an outcome 910 of not being accepted. While at the high end 940 of the S-shaped curve, the grade point average 920 predicts an outcome 910 of being accepted. Logistic regression may be used to predict house values, customer lifetime value in the insurance sector, etc.

A support vector machine (SVM) may be used to sort the data with the margins between two classes as far apart as possible. This is called maximum margin separation. The SVM may account for the support vectors while plotting the hyperplane, unlike linear regression which uses the entire dataset for that purpose.

Figure 10:
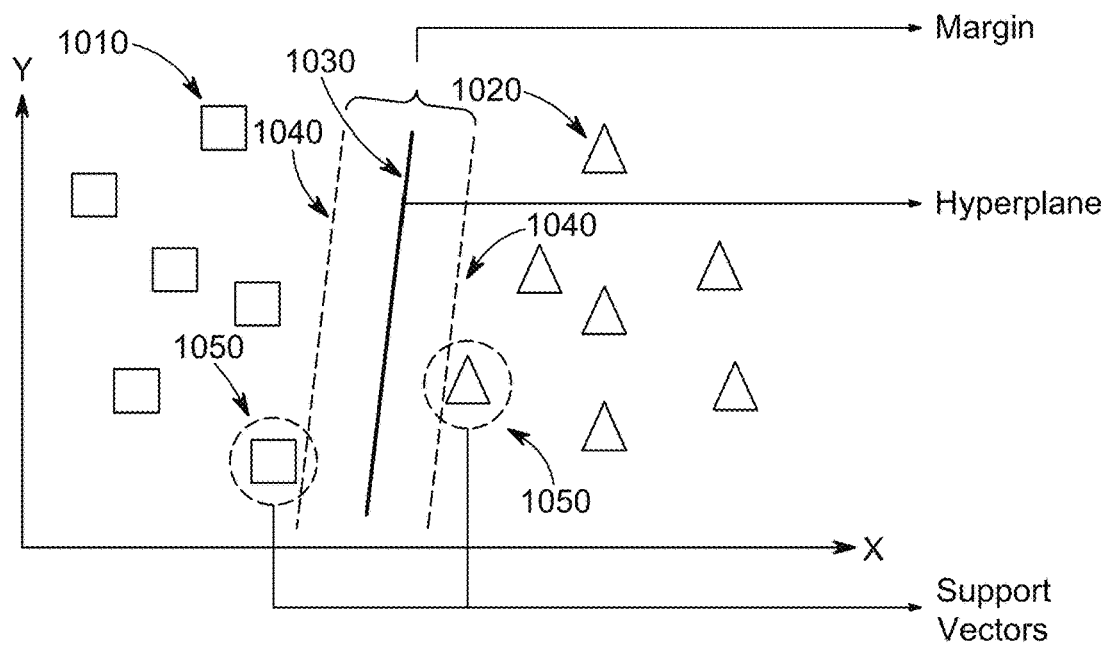
FIG. 10 illustrates an exemplary support vector machine.

FIG. 10 illustrates an exemplary support vector machine. In the exemplary SVM 1000, data may be classified into two different classes represented as squares 1010 and triangles 1020. SVM 1000 operates by drawing a random hyperplane 1030. This hyperplane 1030 is monitored by comparing the distance (illustrated with lines 1040) between the hyperplane 1030 and the closest data points 1050 from each class. The closest data points 1050 to the hyperplane 1030 are known as support vectors. The hyperplane 1030 is drawn based on these support vectors 1050 and an optimum hyperplane has a maximum distance from each of the support vectors 1050. The distance between the hyperplane 1030 and the support vectors 1050 is known as the margin.

SVM 1000 may be used to classify data by using a hyperplane 1030, such that the distance between the hyperplane 1030 and the support vectors 1050 is maximum. Such a SVM 1000 may be used to predict heart disease, for example.

K Nearest Neighbors (KNN) refers to a set of algorithms that generally do not make assumptions on the underlying data distribution, and perform a reasonably short training phase. Generally, KNN uses many data points separated into several classes to predict the classification of a new sample point. Operationally, KNN specifies an integer N with a new sample. The N entries in the model of the system closest to the new sample are selected. The most common classification of these entries is determined and that classification is assigned to the new sample. KNN generally requires the storage space to increase as the training set increases. This also means that the estimation time increases in proportion to the number of training points.

Figure 11:
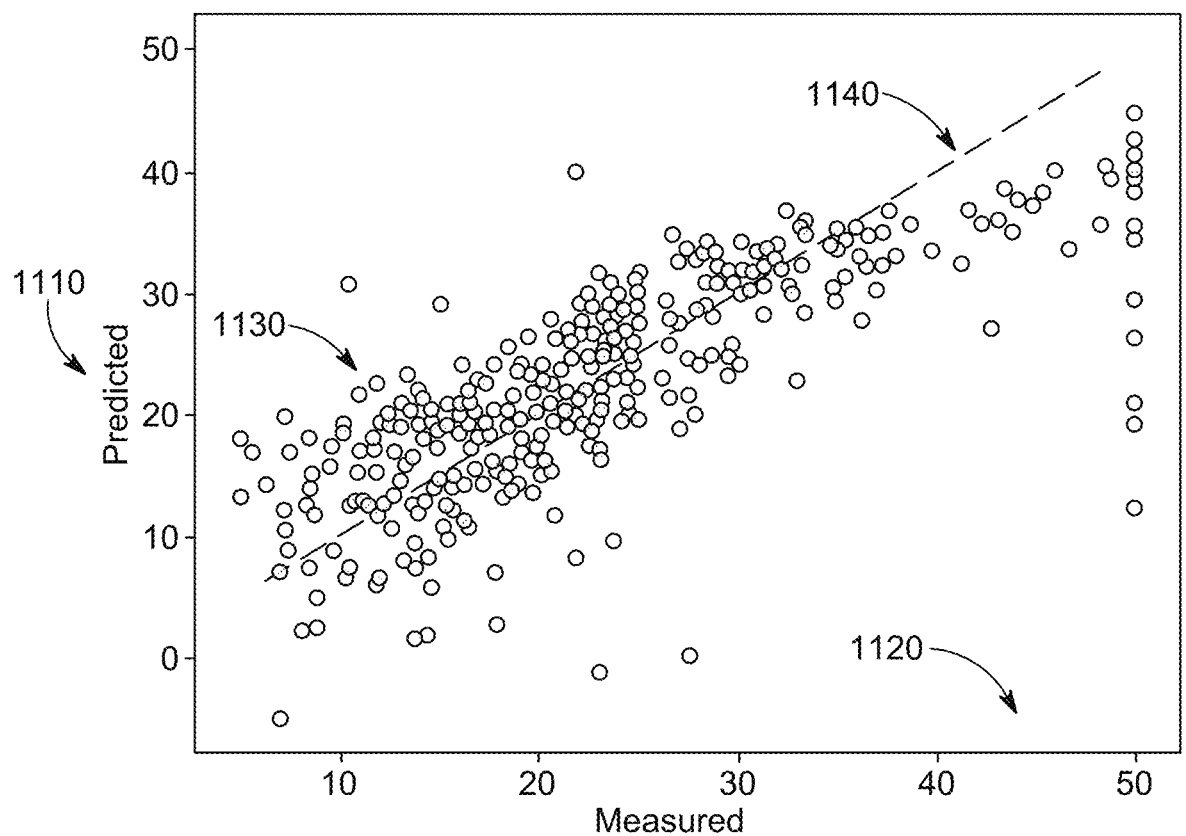
FIG. 11 illustrates an exemplary linear regression model.

In regression algorithms, the output is a continuous quantity so regression algorithms may be used in cases where the target variable is a continuous variable. Linear regression is a general example of regression algorithms. Linear regression may be used to gauge genuine qualities (cost of houses, number of calls, all out deals and so forth) in view of the consistent variable(s). A connection between the variables and the outcome is created by fitting the best line (hence linear regression). This best fit line is known as regression line and spoken to by a direct condition Y=a*X+b. Linear regression is best used in approaches involving a low number of dimensions FIG. 11 illustrates an exemplary linear regression model. In this model, a predicted variable 1110 is modeled against a measured variable 1120. A cluster of instances of the predicted variable 1110 and measured variable 1120 are plotted as data points 1130. Data points 1130 are then fit with the best fit line 1140. Then the best fit line 1140 is used in subsequent predicted, given a measured variable 1120, the line 1140 is used to predict the predicted variable 1110 for that instance. Linear regression may be used to model and predict in a financial portfolio, salary forecasting, real estate and in traffic in arriving at estimated time of arrival.

Clustering algorithms may also be used to model and train on a data set. In clustering, the input is assigned into two or more clusters based on feature similarity. Clustering algorithms generally learn the patterns and useful insights from data without any guidance. For example, clustering viewers into similar groups based on their interests, age, geography, etc. may be performed using unsupervised learning algorithms like K-means clustering.

K-means clustering generally is regarded as a simple unsupervised learning approach. In K-means clustering similar data points may be gathered together and bound in the form of a cluster. One method for binding the data points together is by calculating the centroid of the group of data points. In determining effective clusters, in K-means clustering the distance between each point from the centroid of the cluster is evaluated. Depending on the distance between the data point and the centroid, the data is assigned to the closest cluster. The goal of clustering is to determine the intrinsic grouping in a set of unlabeled data. The 'K' in K-means stands for the number of clusters formed. The number of clusters (basically the number of classes in which new instances of data may be classified) may be determined by the user. This determination may be performed using feedback and viewing the size of the clusters during training, for example.

K-means is used majorly in cases where the data set has points which are distinct and well separated; otherwise, if the clusters are not separated the modeling may render the clusters inaccurate. Also, K-means may be avoided in cases where the data set contains a high amount of outliers or the data set is non-linear.

Figure 12:
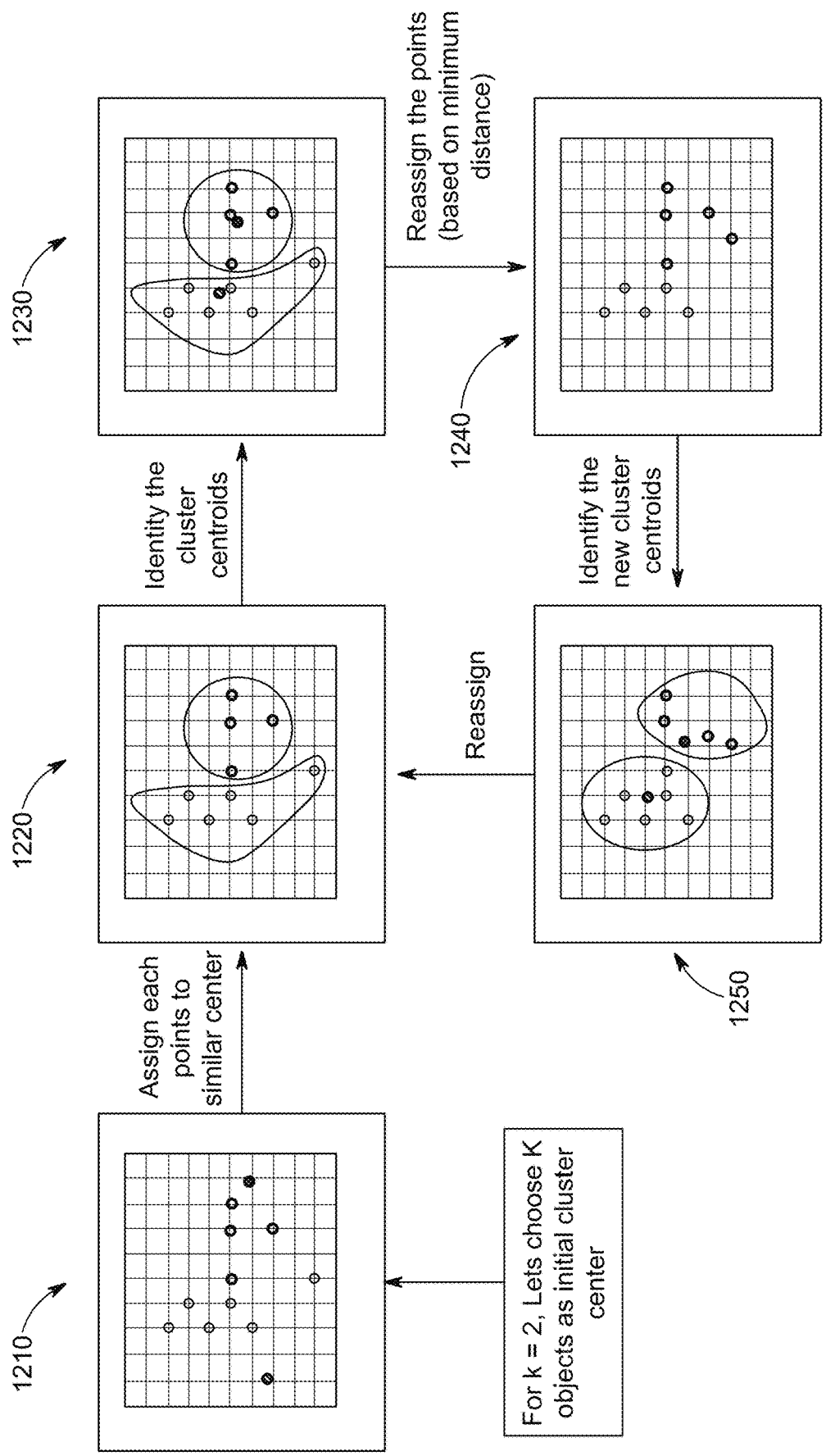
FIG. 12 illustrates an exemplary K-means clustering.

FIG. 12 illustrates a K-means clustering. In K-means clustering, the data points are plotted and the K value is assigned. For example, for K=2 in FIG. 12, the data points are plotted as shown in depiction 1210. The points are then assigned to similar centers at step 1220. The cluster centroids are identified as shown in 1230. Once centroids are identified, the points are reassigned to the cluster to provide the minimum distance between the data point to the respective cluster centroid as illustrated in 1240. Then a new centroid of the cluster may be determined as illustrated in depiction 1250. As the data pints are reassigned to a cluster, new cluster centroids formed, iteration, or series of iterations may occur to enable the clusters to be minimized in size and the centroid of the optimal centroid determined. Then as new data points are measured, the new data points may be compared with the centroid and cluster to identify with that cluster.

Ensemble learning algorithms may be used. These algorithms use multiple learning algorithms to obtain better predictive performance than could be obtained from any of the constituent learning algorithms alone. Ensemble learning algorithms perform the task of searching through a hypothesis space to find a suitable hypothesis that will make good predictions with a particular problem. Even if the hypothesis space contains hypotheses that are very well-suited for a particular problem, it may be very difficult to find a good hypothesis. Ensemble algorithms combine multiple hypotheses to form a better hypothesis. The term ensemble is usually reserved for methods that generate multiple hypotheses using the same base learner. The broader term of multiple classifier systems also covers hybridization of hypotheses that are not induced by the same base learner.

Evaluating the prediction of an ensemble typically requires more computation than evaluating the prediction of a single model, so ensembles may be thought of as a way to compensate for poor learning algorithms by performing a lot of extra computation. Fast algorithms such as decision trees are commonly used in ensemble methods, for example, random forests, although slower algorithms can benefit from ensemble techniques as well.

An ensemble is itself a supervised learning algorithm, because it can be trained and then used to make predictions. The trained ensemble, therefore, represents a single hypothesis. This hypothesis, however, is not necessarily contained within the hypothesis space of the models from which it is built. Thus, ensembles can be shown to have more flexibility in the functions they can represent. This flexibility can, in theory, enable them to over-fit the training data more than a single model would, but in practice, some ensemble techniques (especially bagging) tend to reduce problems related to over-fitting of the training data.

Empirically, ensemble algorithms tend to yield better results when there is a significant diversity among the models. Many ensemble methods, therefore, seek to promote diversity among the models they combine. Although non-intuitive, more random algorithms (like random decision trees) can be used to produce a stronger ensemble than very deliberate algorithms (like entropy-reducing decision trees). Using a variety of strong learning algorithms, however, has been shown to be more effective than using techniques that attempt to dumb-down the models in order to promote diversity.

The number of component classifiers of an ensemble has a great impact on the accuracy of prediction. A priori determining of ensemble size and the volume and velocity of big data streams make this even more crucial for online ensemble classifiers. A theoretical framework suggests that there are an ideal number of component classifiers for an ensemble such that having more or less than this number of classifiers would deteriorate the accuracy. The theoretical framework shows that using the same number of independent component classifiers as class labels gives the highest accuracy.

Figure 13:
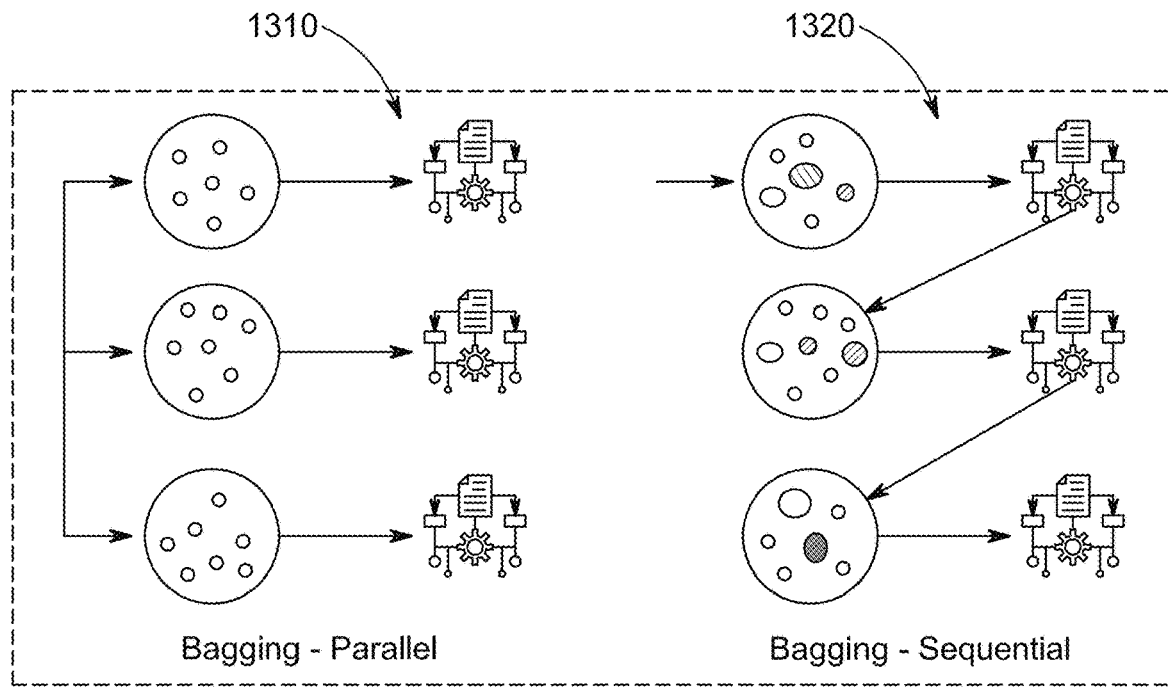
FIG. 13 illustrates an exemplary ensemble learning algorithm.

Some common types of ensembles include Bayes optimal classifier, bootstrap aggregating (bagging), boosting, Bayesian model averaging, Bayesian model combination, bucket of models and stacking. FIG. 13 illustrates an exemplary ensemble learning algorithm where bagging is being performed in parallel 1310 and boosting is being performed sequentially 1320.

A neural network is a network or circuit of neurons, or in a modern sense, an artificial neural network, composed of artificial neurons or nodes. The connections of the biological neuron are modeled as weights. A positive weight reflects an excitatory connection, while negative values mean inhibitory connections. Inputs are modified by a weight and summed using a linear combination. An activation function may control the amplitude of the output. For example, an acceptable range of output is usually between 0 and 1, or it could be −1 and 1.

These artificial networks may be used for predictive modeling, adaptive control and applications and can be trained via a dataset. Self-learning resulting from experience can occur within networks, which can derive conclusions from a complex and seemingly unrelated set of information.

For completeness, a biological neural network is composed of a group or groups of chemically connected or functionally associated neurons. A single neuron may be connected to many other neurons and the total number of neurons and connections in a network may be extensive. Connections, called synapses, are usually formed from axons to dendrites, though dendrodendritic synapses and other connections are possible. Apart from the electrical signaling, there are other forms of signaling that arise from neurotransmitter diffusion.

Artificial intelligence, cognitive modeling, and neural networks are information processing paradigms inspired by the way biological neural systems process data. Artificial intelligence and cognitive modeling try to simulate some properties of biological neural networks. In the artificial intelligence field, artificial neural networks have been applied successfully to speech recognition, image analysis and adaptive control, in order to construct software agents (in computer and video games) or autonomous robots.

A neural network (NN), in the case of artificial neurons called artificial neural network (ANN) or simulated neural network (SNN), is an interconnected group of natural or artificial neurons that uses a mathematical or computational model for information processing based on a connectionistic approach to computation. In most cases an ANN is an adaptive system that changes its structure based on external or internal information that flows through the network. In more practical terms neural networks are non-linear statistical data modeling or decision making tools. They can be used to model complex relationships between inputs and outputs or to find patterns in data.

An artificial neural network involves a network of simple processing elements (artificial neurons) which can exhibit complex global behavior, determined by the connections between the processing elements and element parameters.

One classical type of artificial neural network is the recurrent Hopfield network. The utility of artificial neural network models lies in the fact that they can be used to infer a function from observations and also to use it. Unsupervised neural networks can also be used to learn representations of the input that capture the salient characteristics of the input distribution, and more recently, deep learning algorithms, which can implicitly learn the distribution function of the observed data. Learning in neural networks is particularly useful in applications where the complexity of the data or task makes the design of such functions by hand impractical.

Neural networks can be used in different fields. The tasks to which artificial neural networks are applied tend to fall within the following broad categories: function approximation, or regression analysis, including time series prediction and modeling; classification, including pattern and sequence recognition, novelty detection and sequential decision making, data processing, including filtering, clustering, blind signal separation and compression.

Application areas of ANNs include nonlinear system identification and control (vehicle control, process control), game-playing and decision making (backgammon, chess, racing), pattern recognition (radar systems, face identification, object recognition), sequence recognition (gesture, speech, handwritten text recognition), medical diagnosis, financial applications, data mining (or knowledge discovery in databases, "KDD"), visualization and e-mail spam filtering. For example, it is possible to create a semantic profile of user's interests emerging from pictures trained for object recognition.

Figure 14:
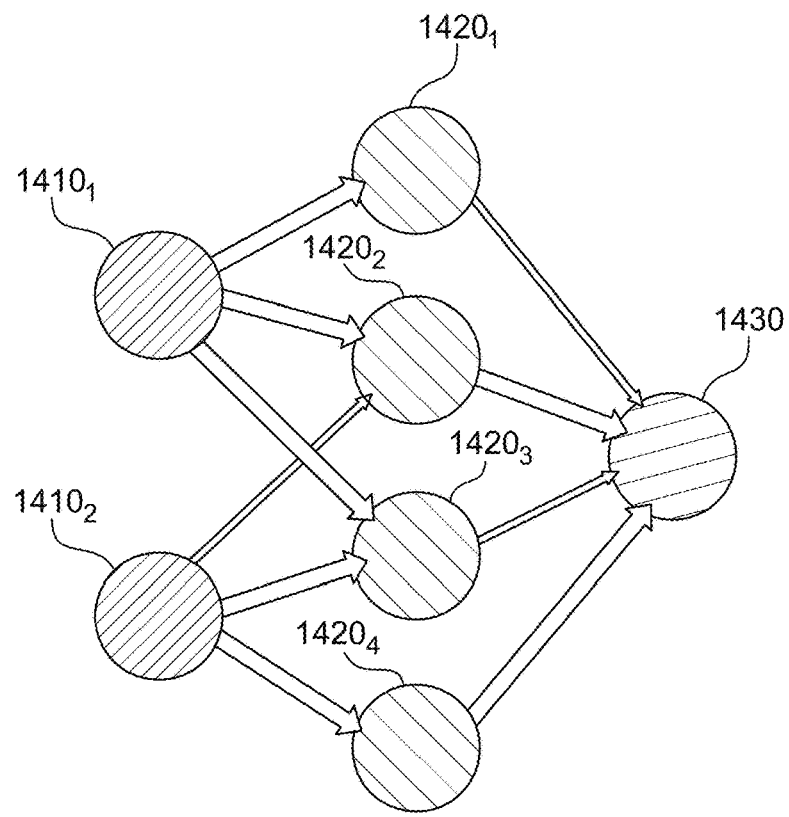
FIG. 14 illustrates an exemplary neural network.

FIG. 14 illustrates an exemplary neural network. In the neural network there is an input layer represented by a plurality of inputs, such as $1410_1$ and $1410_2$. The inputs $1410_1$, $1410_2$ are provided to a hidden layer depicted as including nodes $1420_1$, $1420_2$, $1420_3$, $1420_4$. These nodes $1420_1$, $1420_2$, $1420_3$, $1420_4$ are combined to produce an output 1430 in an output layer. The neural network performs simple processing via the hidden layer of simple processing elements, nodes $1420_1$, $1420_2$, $1420_3$, $1420_4$, which can exhibit complex global behavior, determined by the connections between the processing elements and element parameters.

Figure 15:
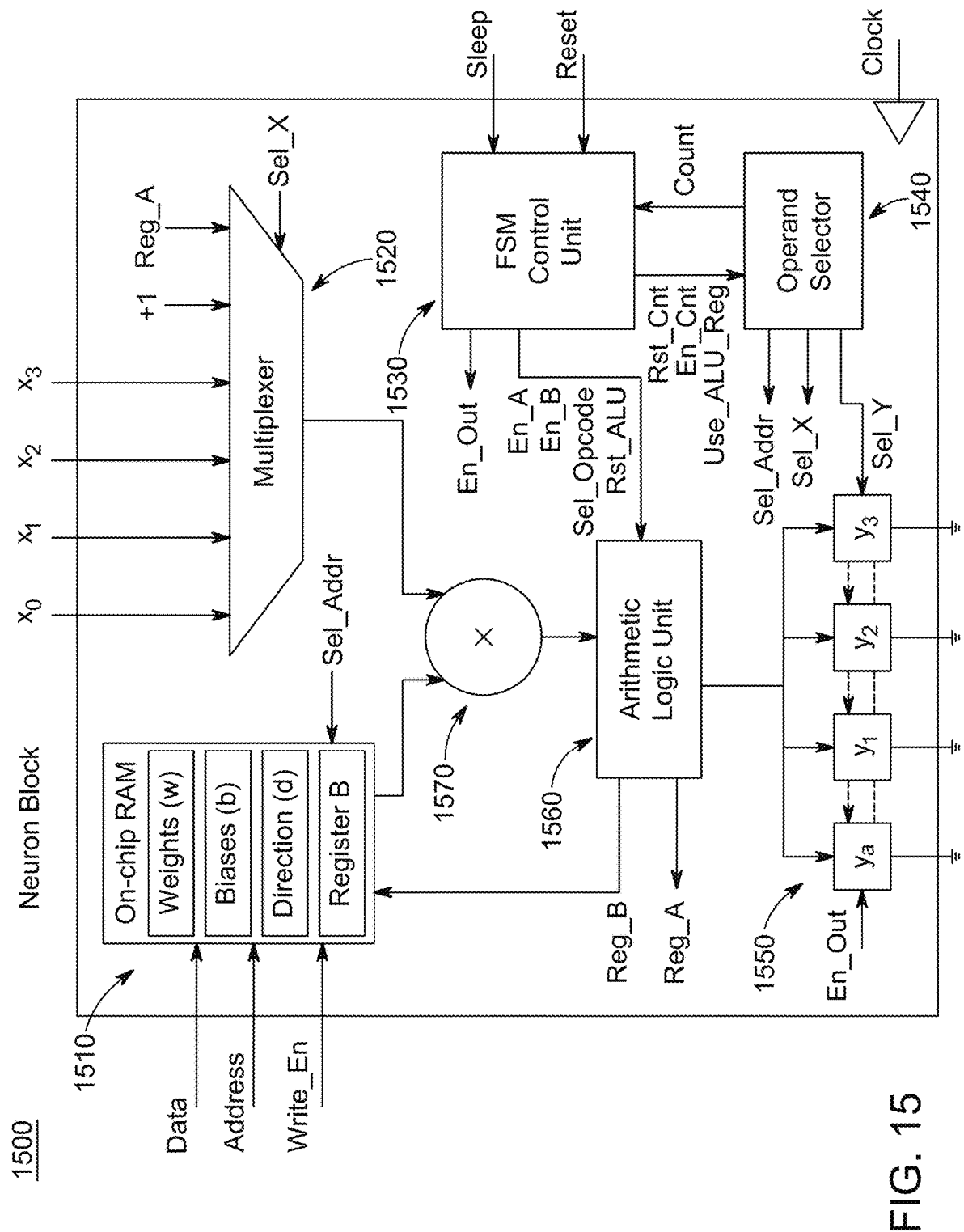
FIG. 15 illustrates a hardware based neural network.

The neural network of FIG. 14 may be implemented in hardware. As depicted in FIG. 15, a hardware based neural network is depicted.

Cardiac arrhythmias and atrial fibrillation in particular, persist as common and dangerous medical ailments, especially in the aging population. In patients with normal sinus rhythm, the heart, which is comprised of atrial, ventricular, and excitatory conduction tissue, is electrically excited to beat in a synchronous, patterned fashion. In patients with cardiac arrhythmias, abnormal regions of cardiac tissue do not follow the synchronous beating cycle associated with normally conductive tissue as in patients with normal sinus rhythm. Instead, the abnormal regions of cardiac tissue aberrantly conduct to adjacent tissue, thereby disrupting the cardiac cycle into an asynchronous cardiac rhythm. Such abnormal conduction has been previously known to occur at various regions of the heart, for example, in the region of the sino-atrial (SA) node, along the conduction pathways of the atrioventricular (AV) node and the Bundle of His, or in the cardiac muscle tissue forming the walls of the ventricular and atrial cardiac chambers.

Cardiac arrhythmias, including atrial arrhythmias, may be of a multiwavelet reentrant type, characterized by multiple asynchronous loops of electrical impulses that are scattered about the atrial chamber and are often self-propagating. Alternatively, or in addition to the multiwavelet reentrant type, cardiac arrhythmias may also have a focal origin, such as when an isolated region of tissue in an atrium fires autonomously in a rapid, repetitive fashion. Ventricular tachycardia (V-tach or VT) is a tachycardia, or fast heart rhythm that originates in one of the ventricles of the heart. This is a potentially life-threatening arrhythmia because it may lead to ventricular fibrillation and sudden death.

One type of arrhythmia, atrial fibrillation, occurs when the normal electrical impulses generated by the sinoatrial node are overwhelmed by disorganized electrical impulses that originate in the atria and pulmonary veins causing irregular impulses to be conducted to the ventricles. An irregular heartbeat results and may last from minutes to weeks, or even years. Atrial fibrillation (AF) is often a chronic condition that leads to a small increase in the risk of death often due to strokes. Risk increases with age. Approximately 8% of people over 80 have some amount of AF. Atrial fibrillation is often asymptomatic and is not in itself generally life-threatening, but it may result in palpitations, weakness, fainting, chest pain and congestive heart failure. Stroke risk increases during AF because blood may pool and form clots in the poorly contracting atria and the left atrial appendage.

The first line of treatment for AF is medication that either slows the heart rate or reverts the heart rhythm back to normal. Additionally, persons with AF are often given anticoagulants to protect them from the risk of stroke. The use of such anticoagulants comes with its own risk of internal bleeding. In some patients, medication is not sufficient and their AF is deemed to be drug-refractory, i.e., untreatable with standard pharmacological interventions. Synchronized electrical cardioversion may also be used to convert AF to a normal heart rhythm. Alternatively, AF patients are treated by catheter ablation.

A catheter ablation based treatment may include mapping the electrical properties of heart tissue, especially the endocardium and the heart volume, and selectively ablating cardiac tissue by application of energy. Cardiac mapping, for example, creating a map of electrical potentials (a voltage map) of the wave propagation along the heart tissue or a map of arrival times (a local time activation (LAT) map) to various tissue located points, may be used for detecting local heart tissue dysfunction ablations, such as those based on cardiac mapping, can cease or modify the propagation of unwanted electrical signals from one portion of the heart to another.

The ablation process damages the unwanted electrical pathways by formation of non-conducting lesions. Various energy delivery modalities have been disclosed for forming lesions, and include use of microwave, laser and more commonly, radiofrequency energies to create conduction blocks along the cardiac tissue wall. In a two-step procedure-mapping followed by ablation-electrical activity at points within the heart is typically sensed and measured by advancing a catheter containing one or more electrical sensors (or electrodes) into the heart, and acquiring data at a multiplicity of points. These data are then utilized to select the endocardial target areas at which ablation are to be performed.

Cardiac ablation and other cardiac electrophysiological procedures have become increasingly complex as clinicians treat challenging conditions such as atrial fibrillation and ventricular tachycardia. The treatment of complex arrhythmias can now rely on the use of three dimensional (3D) mapping systems in order to reconstruct the anatomy of the heart chamber of interest.

For example, cardiologists rely upon software such as the Complex Fractionated Atrial Electrograms (CFAE) module of the CARTO@3 3D mapping system, produced by Biosense Webster, Inc. (Diamond Bar, Calif.), to analyze intra-cardiac EGM signals and determine the ablation points for treatment of a broad range of cardiac conditions, including atypical atrial flutter and ventricular tachycardia.

The 3D maps can provide multiple pieces of information regarding the electrophysiological properties of the tissue that represent the anatomical and functional substrate of these challenging arrhythmias.

Cardiomyopathies with different etiologies (ischemic, dilated cardiomyopathy (DCM), hypertrophic cardiomyopathy (HCM), arrhythmogenic right ventricular dysplasia (ARVD), left ventricular non-compaction (LVNC), etc.) have an identifiable substrate, featured by areas of unhealthy tissue surrounded by areas of normally functioning cardiomyocytes.

Figure 16:
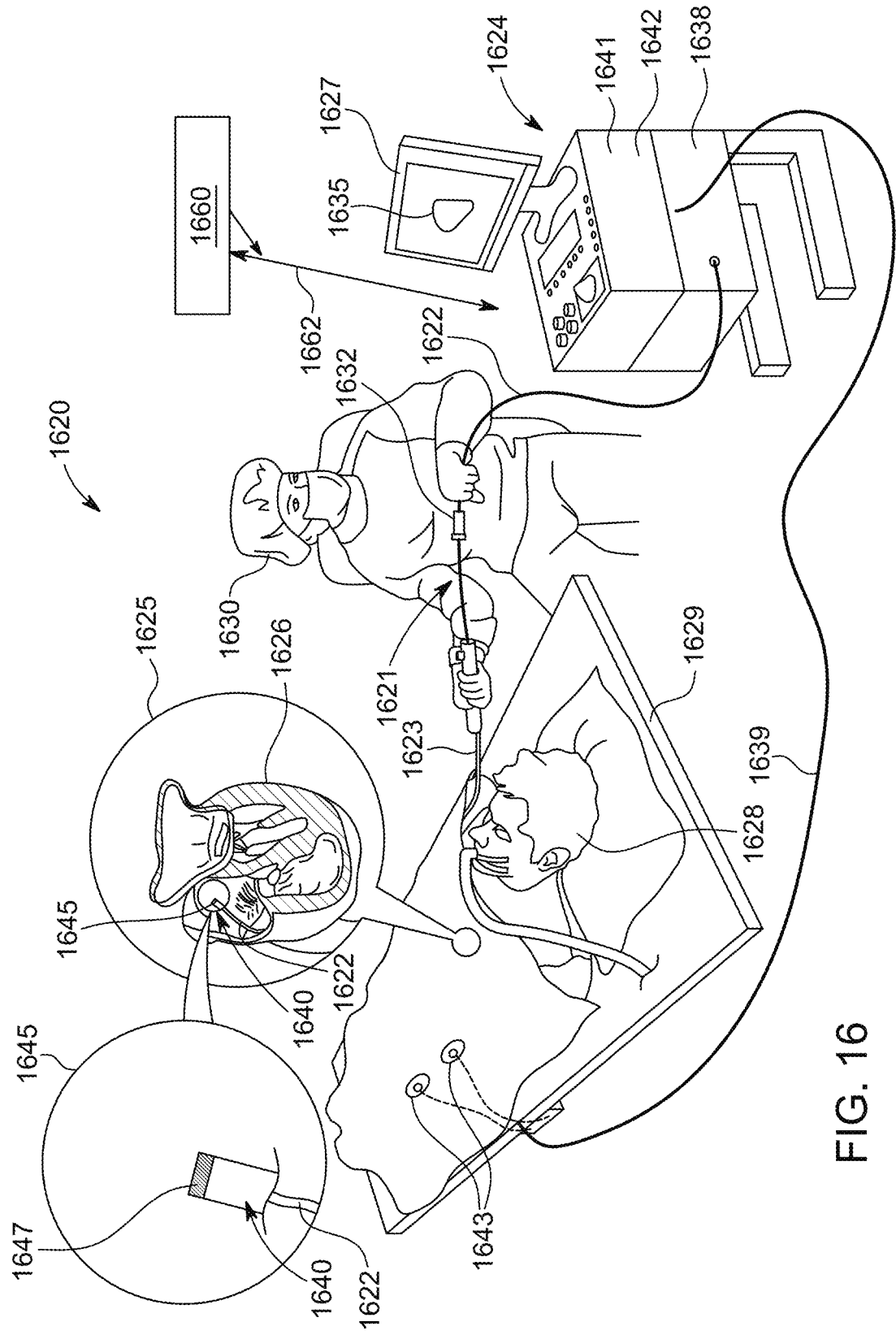
FIG. 16 is a diagram of an exemplary system in which one or more features of the disclosed subject matter can be implemented.

FIG. 16 is a diagram of an exemplary system 1620 in which one or more features of the disclosure subject matter can be implemented. All or parts of system 1620 may be used to collect information for a training dataset and/or all or parts of system 1620 may be used to implement a trained model. System 1620 may include components, such as a catheter 1640, that are configured to damage tissue areas of an intra-body organ. The catheter 1640 may also be further configured to obtain biometric data. Although catheter 1640 is shown to be a point catheter, it will be understood that a catheter of any shape that includes one or more elements (e.g., electrodes) may be used to implement the embodiments disclosed herein. System 1620 includes a probe 1621, having shafts that may be navigated by a physician 1630 into a body part, such as heart 1626, of a patient 1628 lying on a table 1629. According to embodiments, multiple probes may be provided, however, for purposes of conciseness, a single probe 1621 is described herein but it will be understood that probe 1621 may represent multiple probes. As shown in FIG. 16, physician 1630 may insert shaft 1622 through a sheath 1623, while manipulating the distal end of the shafts 1622 using a manipulator 1632 near the proximal end of the catheter 1640 and/or deflection from the sheath 1623. As shown in an inset 1625, catheter 1640 may be fitted at the distal end of shafts 1622. Catheter 1640 may be inserted through sheath 1623 in a collapsed state and may be then expanded within heart 1626. Cather 1640 may include at least one ablation electrode 1647 and a catheter needle 1648, as further disclosed herein.

According to exemplary embodiments, catheter 1640 may be configured to ablate tissue areas of a cardiac chamber of heart 1626. Inset 1645 shows catheter 1640 in an enlarged view, inside a cardiac chamber of heart 1626. As shown, catheter 1640 may include at least one ablation electrode 1647 coupled onto the body of the catheter. According to other exemplary embodiments, multiple elements may be connected via splines that form the shape of the catheter 1640. One or more other elements (not shown) may be provided and may be any elements configured to ablate or to obtain biometric data and may be electrodes, transducers, or one or more other elements.

According to embodiments disclosed herein, the ablation electrodes, such as electrode 1647, may be configured to provide energy to tissue areas of an intra-body organ such as heart 1626. The energy may be thermal energy and may cause damage to the tissue area starting from the surface of the tissue area and extending into the thickness of the tissue area.

According to exemplary embodiments disclosed herein, biometric data may include one or more of LATs, electrical activity, topology, bipolar mapping, dominant frequency, impedance, or the like. The local activation time may be a point in time of a threshold activity corresponding to a local activation, calculated based on a normalized initial starting point. Electrical activity may be any applicable electrical signals that may be measured based on one or more thresholds and may be sensed and/or augmented based on signal to noise ratios and/or other filters. A topology may correspond to the physical structure of a body part or a portion of a body part and may correspond to changes in the physical structure relative to different parts of the body part or relative to different body parts. A dominant frequency may be a frequency or a range of frequency that is prevalent at a portion of a body part and may be different in different portions of the same body part. For example, the dominant frequency of a pulmonary vein of a heart may be different than the dominant frequency of the right atrium of the same heart. Impedance may be the resistance measurement at a given area of a body part.

As shown in FIG. 16, the probe 1621, and catheter 1640 may be connected to a console 1624. Console 1624 may include a processor 1641, such as a general-purpose computer, with suitable front end and interface circuits 1638 for transmitting and receiving signals to and from catheter, as well as for controlling the other components of system 1620. In some embodiments, processor 1641 may be further configured to receive biometric data, such as electrical activity, and determine if a given tissue area conducts electricity. According to an embodiment, the processor may be external to the console 1624 and may be located, for example, in the catheter, in an external device, in a mobile device, in a cloud-based device, or may be a standalone processor.

Processor 1641 may include a general-purpose computer, which may be programmed in software to carry out the functions described herein. The software may be downloaded to the general-purpose computer in electronic form, over a network, for example, or it may, alternatively or additionally, be provided and/or stored on non-transitory tangible media, such as magnetic, optical, or electronic memory. The example configuration shown in FIG. 16 may be modified to implement the embodiments disclosed herein. The disclosed embodiments may similarly be applied using other system components and settings. Additionally, system 1620 may include additional components, such as elements for sensing electrical activity, wired or wireless connectors, processing and display devices, or the like.

According to an embodiment, a display connected to a processor (e.g., processor 1641) may be located at a remote location such as a separate hospital or in separate healthcare provider networks. Additionally, the system 1620 may be part of a surgical system that is configured to obtain anatomical and electrical measurements of a patient's organ, such as a heart, and performing a cardiac ablation procedure. An example of such a surgical system is the Carto® system sold by Biosense Webster.

The system 1620 may also, and optionally, obtain biometric data such as anatomical measurements of the patient's heart using ultrasound, computed tomography (CT), magnetic resonance imaging (MRI) or other medical imaging techniques known in the art. The system 1620 may obtain electrical measurements using catheters, electrocardiograms (EKGs) or other sensors that measure electrical properties of the heart. The biometric data including anatomical and electrical measurements may then be stored in a memory 1642 of the mapping system 1620, as shown in FIG. 16. The biometric data may be transmitted to the processor 1641 from the memory 1642. Alternatively, or in addition, the biometric data may be transmitted to a server 1660, which may be local or remote, using a network 1662.

Network 1662 may be any network or system generally known in the art such as an intranet, a local area network (LAN), a wide area network (WAN), a metropolitan area network (MAN), a direct connection or series of connections, a cellular telephone network, or any other network or medium capable of facilitating communication between the mapping system 1620 and the server 1660. The network 1662 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 1662.

In some instances, the server 1662 may be implemented as a physical server. In other instances, server 1662 may be implemented as a virtual server a public cloud computing provider (e.g., Microsoft Azure, Amazon Web Services (AWS) @).

Control console 1624 may be connected, by a cable 1639, to body surface electrodes 1643, which may include adhesive skin patches that are affixed to the patient 1628. The processor, in conjunction with a current tracking module, may determine position coordinates of the catheter 1640 inside the body part (e.g., heart 1626) of a patient. The position coordinates may be based on impedances or electromagnetic fields measured between the body surface electrodes 1643 and the electrode 1648 or other electromagnetic components of the catheter 40. Additionally or alternatively, location pads may be located on the surface of bed 1629 and may be separate from the bed 1629.

Processor 1641 may include real-time noise reduction circuitry typically configured as a field programmable gate array (FPGA), followed by an analog-to-digital (A/D) ECG (electrocardiograph) or EMG (electromyogram) signal conversion integrated circuit. The processor 1641 may pass the signal from an A/D ECG or EMG circuit to another processor and/or can be programmed to perform one or more functions disclosed herein.

Control console 1624 may also include an input/output (I/O) communications interface that enables the control console to transfer signals from, and/or transfer signals to electrode 47.

During a procedure, processor 1641 may facilitate the presentation of a body part rendering 1635 to physician 1630 on a display 1627, and store data representing the body part rendering 1635 in a memory 1642. Memory 1642 may comprise any suitable volatile and/or non-volatile memory, such as random-access memory or a hard disk drive. In some embodiments, medical professional 1630 may be able to manipulate a body part rendering 1635 using one or more input devices such as a touch pad, a mouse, a keyboard, a gesture recognition apparatus, or the like. For example, an input device may be used to change the position of catheter 1640 such that rendering 1635 is updated. In alternative embodiments, display 1627 may include a touchscreen that can be configured to accept inputs from medical professional 1630, in addition to presenting a body part rendering 1635.

During a real or virtual procedure, the present system may collect the entirety of the data related to the procedure. This may include all positions of the device(s), all of the measurements and all of the supplied treatments. In addition, the system may collect any analysis that is performed that preceded the procedure, or during the procedure, plus any measurements after the procedure occurs. This may include analysis presented to the operator, and any internal analysis performed. By way of example, this data may include the catheter position, all of the recorded ECG, impedance measurements, contact information, ultrasound images, X-ray images, information on the energy delivered during the procedure including information such as the power, the generated temperature and impedance before, during and after application. Analysis may include all of the mappings, the stability parameters, presented images and calculations. For example, biometric data may include one or more of LATs, electrical activity, topology, bipolar mapping, dominant frequency, impedance, or the like.

Each procedure, or a series of procedures, including all recorded procedures, may be analyzed. The analysis may include examining the parameters of the procedure(s) to determine how the procedure can be improved. This may include applying any of the methods from FIGS. 4-15. By way of example, in calculating improvements, the step may be performed similar to a cyclist who records heart rate and pedal rate during a ride, and then analysis the data to determine where additional or decreased exertion may be exercised to optimize power and improve the outcome of a ride.

In a specific embodiment, with a procedure designed to improve wide area circumferential ablation (WACA), the WACA generation is performed in the following stages: many points of ablation, testing the isolation of the vain, and closing the gaps. The CARTO presents ablation points that were taken and the ablation index value. In performing analysis, the steps of identifying the points in the first path, presenting in a different color the points that were added, and presenting the details of the points that were taken before, determining why these points were not good enough, e.g., the catheter during that time was not stable and/or the force was not constant. This analysis may contribute to the physician ablation techniques, when during the producer the physician needs to focus on treatment of the patient.

In another specific embodiment for improving the finding of channels in scar, the electrically conductive gaps in the ablations, the system records ECG data including the voltage and the LAT, and by analyzing the maps, the activation velocity, like in CARTO. Using the system offline from a procedure, a simulation may be started that mimics what happened if a premature bit start in each position to teach about the techniques to analysis where it is important to ablate to generate better techniques of ablation.

In the system, all data is good, and the analysis via FIGS. 4-15 is necessary to determine what data is useful. The recordation of as much data as is possible and after the procedure via the described techniques above an analysis algorithm may be developed, allowing an understanding of the useful data. After the algorithm is defined, a focus on aspects of the data may occur allowing a subset of the data going forward to be collected.

Figure 17:
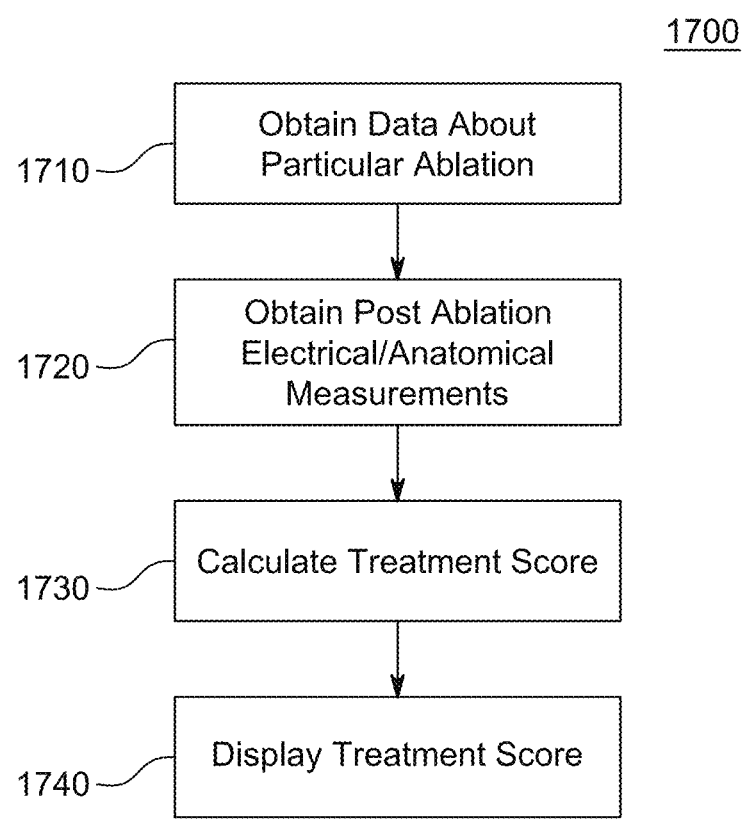
FIG. 17 illustrates a process for scoring a cardiac ablation treatment according to certain embodiments.

FIG. 17 illustrates a process 1700 for scoring a cardiac ablation treatment according to certain embodiments. At step 1710, the electrical and anatomical measurements, the mappings and the information about a particular ablation procedure are retrieved. In some instances, the information is retrieved from the cloud-based platform 160, and in other instances, the information is retrieved from the local server 120, and in further instances some information may be retrieved from either or both cloud-based platform 160 and local server 120.

At step 1720, the post-ablation electrical and anatomical measurements are retrieved for the particular ablation procedure. At step 1730, a treatment score is generated by comparing the post-ablation electrical and anatomical measurements, the electrical and anatomical measurements, the mappings and the information about a particular ablation procedure with previously performed procedures. In some instances, the comparison is performed using the machine learning of the local server 120 based on the data stored in the local database. In other instances, the comparison is performed using the machine learning of the cloud-based platform based on the anonymized data stored in the anonymized database. At step 1740, the treatment score calculated in 1740 is displayed.

Figure 18:
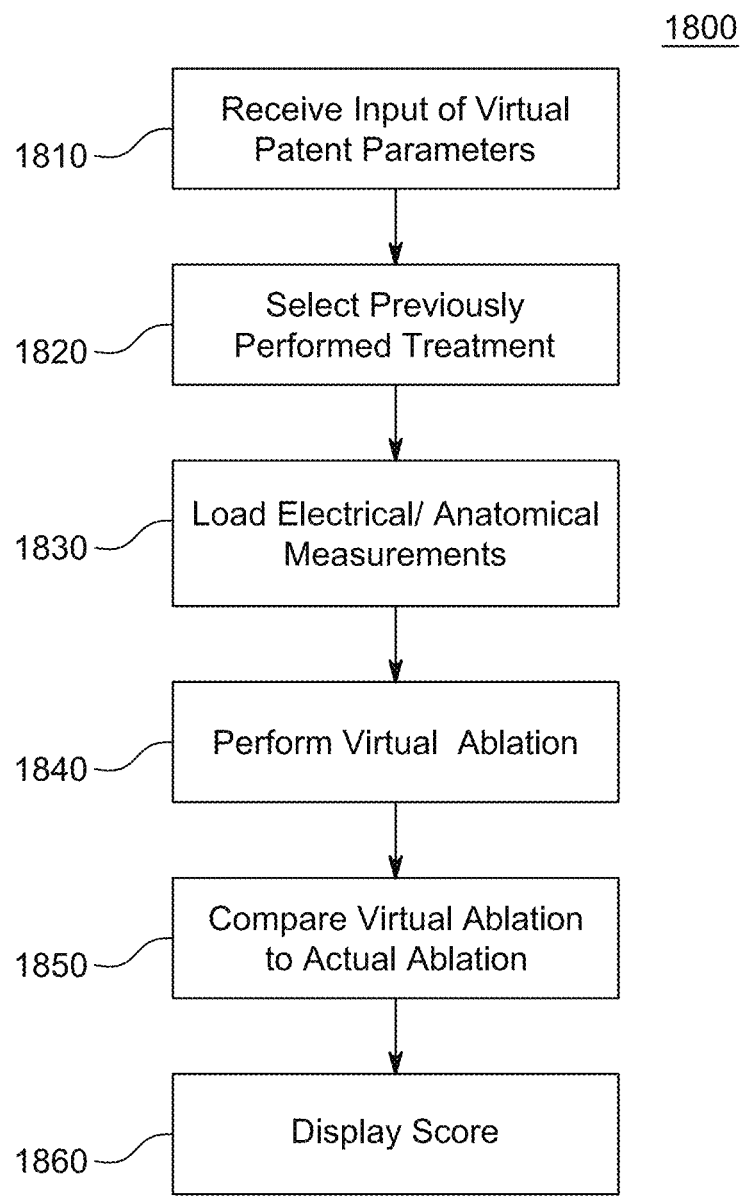
FIG. 18 illustrates a process for training a surgeon to perform a cardiac ablation using an AR/VR system according to certain embodiments.

FIG. 18 illustrates a process 1800 for training a surgeon to perform a cardiac ablation using an AR/VR system according to certain embodiments. At step 1810, the trainee (e.g., surgeon training) enters parameters about the heart to practice on. Example parameters may include particular cardiac anomalies or the age and gender of the patient. These parameters can come from both the patient medical record including imaging (CT/MR) data, halter data, and from the early stages of the procedure that includes electro-anatomical data.

At step 1820, the anonymized database of the cloud-based platform 160 is queried for a cardiac ablation that matches the parameters and a particular cardiac ablation is selected based on the query. At step 1830, the electrical and anatomical measurements of the selected ablation are loaded into the AR/VR system. Once loaded in the AR/VR system, the trainee performs the cardiac ablation at step 1840 according to a virtual ablation plan. In some instances, the trainee may be prompted to select among a plurality of virtual ablation plans. At step 1850, the AR/VR system compares the performance of the trainee with the results of the surgeon that performed the selected cardiac ablation. At step 1860, a score is calculated and displayed by the AR/VR system based on the comparison in 1850.

Figure 19A:
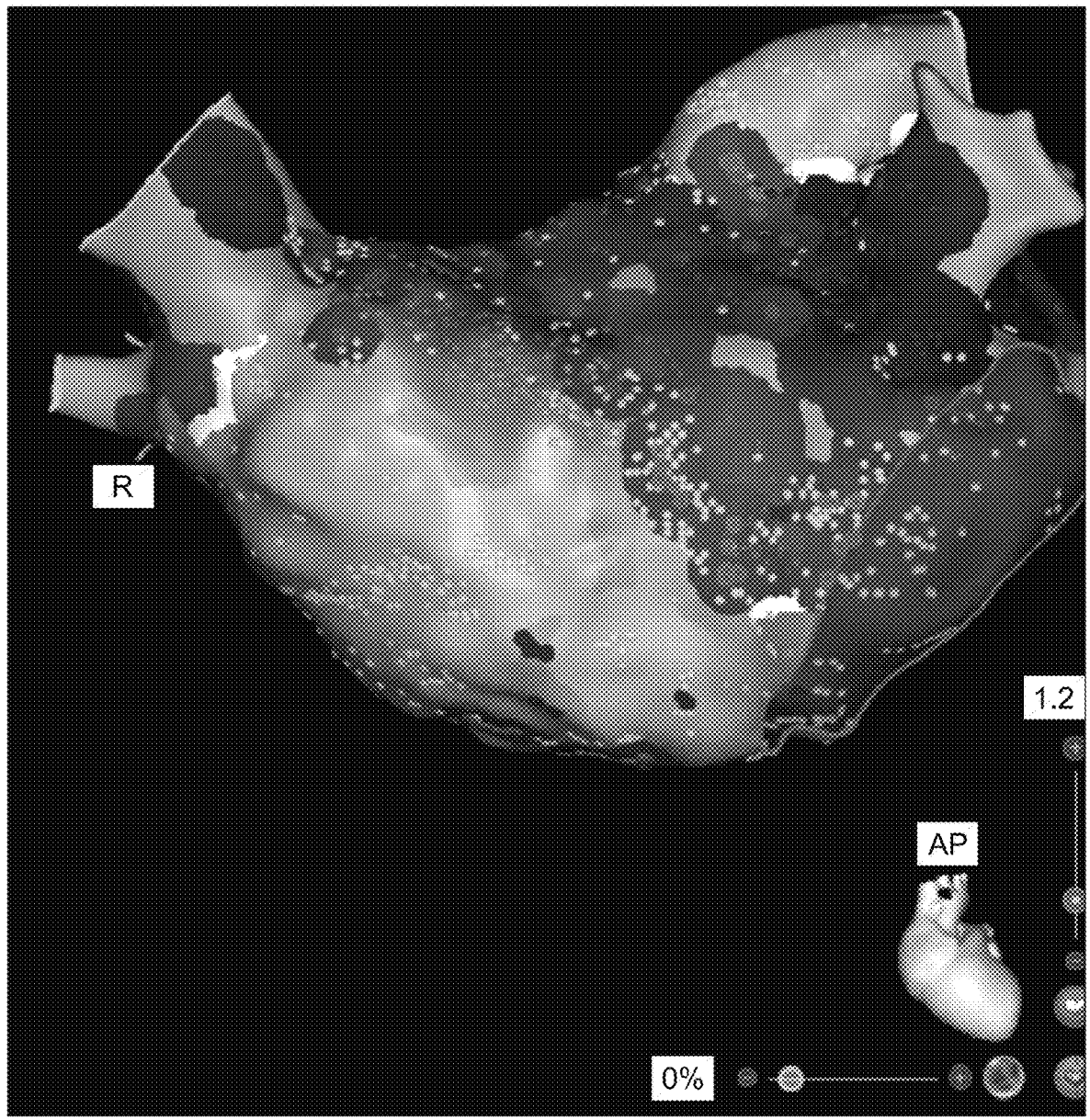
FIG. 19A illustrates an example of a mapping that can be generated by the surgical system.

FIG. 19A illustrates an example of a mapping 1900A that can be generated by the surgical system 110. As previously noted, the mapping 1900A is formed from the detailed anatomical and electrical map of a patient's heart. By comparing the present patient's mapping with the library of mappings of other patients, the system can determine the similarities and differences between the present patient's mapping and those in the library. The system may then determine the mappings in the patient library that provided or resulted in the best treatment outcomes for a condition similar to the present patient's condition. Based on this information, the system may use the determined stored mappings in order to calculate the best treatment plan for the present patient. In a similar manner, as the treatment plan is carried out for the present patient, the system records the ablation treatment and adds this information to the patient library. Once the present patient outcome is determined, the outcome is added to the library.

FIG. 19A represents a standard CARTO® mapping 1900A. The voluminous number of dots shown in the image represent locations where points were taken during the procedure, scars (the darker spots) from areas where material was ablated and the operation progress represented by the other shades.

Figure 19B:
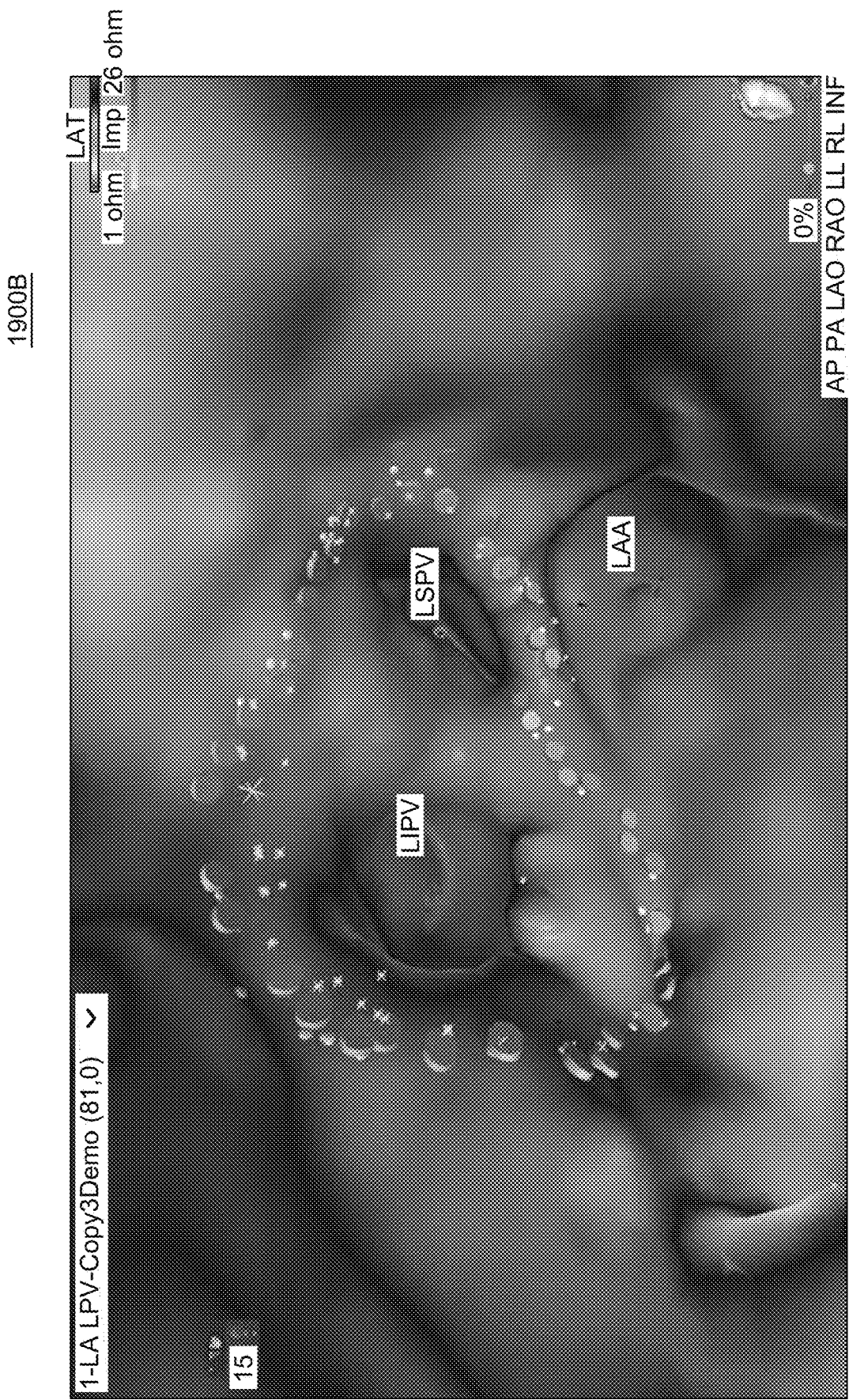
FIG. 19B illustrates an example of a mapping that can be generated by the surgical system.

FIG. 19B illustrates an example of a mapping 1900B that can be generated by the surgical system 110. As previously noted, the mapping 1900B is formed from the detailed anatomical and electrical map of a patient's heart. Mapping 1900B illustrates additional detail and higher resolution view of the ablation points from the procedure. The ablation index is shown and the position related to two pulmonary veins (LIPV and LSPV) is provided. The left atrial appendage (LAA) is also illustrated. These details provide the relation of the ablation to the anatomy.

Figure 19C:
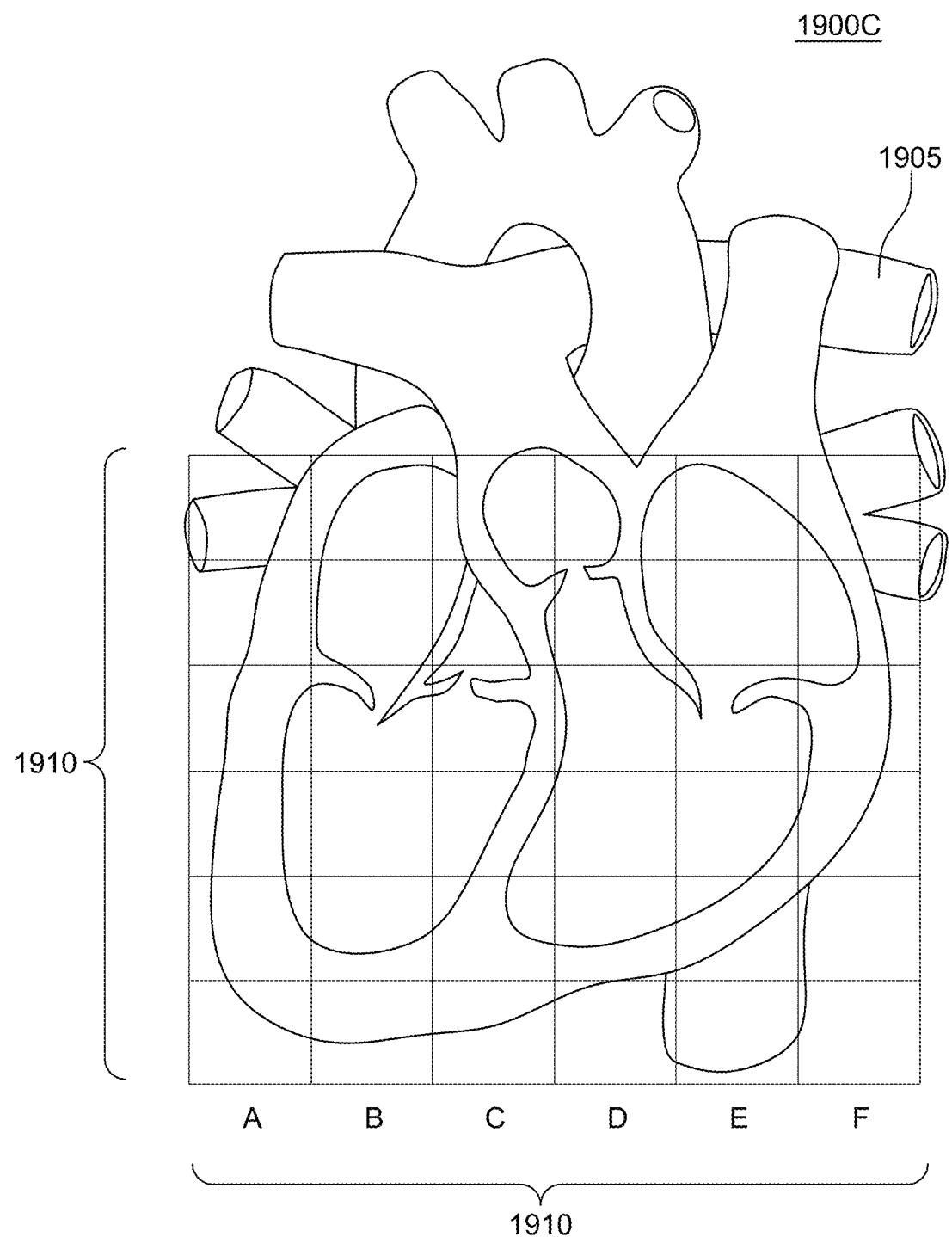
FIG. 19C illustrates another example of a mapping that can be generated by the surgical system.

FIG. 19C illustrates a schematic of another example of a mapping 1900B that can be generated by the surgical system 110. As previously noted, the mapping 1900C is formed from the detailed anatomical and electrical map of a patient's heart. By comparing the present patient's mapping with the library of mappings of other patients, the system can determine similarities and differences between the present patient's mapping and those found in the library.

The mapping 1900C includes a horizontal-vertical grid 1910 that is superimposed on the image of the patient's heart 1905. In some instances, the sizes of the cells in the horizontal-vertical grid 1910 are fixed (e.g., 1 mm×1 mm). In other instances, the horizontal-vertical grid 1910 contains a predetermined number of cells and the sizes of the individual cells are scaled based on the size of the patient's heart.

As discussed herein, the present system 10 provides the ability to collect retrospective anonymized data from a plurality of hospitals to generate an AI algorithm designed to identify potential gaps in the WACA. System 10 provides continuity improvement of the WACA by training. The present system 10 provides physicians detailed analysis of the data to enable ones of the physicians to know how (and where) to improve. The areas of improvement may include improving the WACA ablation quality, including generating better ablation in the first path. System 10 may lead to reducing the probability for case redo, and reducing the need to close the gaps after testing by adenosine stimulation.

The system receives data in the proper context, such as a pair of patients with Paroxysmal atrial fibrillation in the first case plus a redo procedure, for example. The analysis may be viewed and the physician enabled to visualize, such as through AR/VR, the aspects of the procedure that lead to less than ideal ablation, e.g., stability. In this way, the physician can understand how to improve by improving the stability in the exemplary situation described. The system may support tagging the data, such as by performing an initial tagging. Corrections and approval from the physician or other staff may be required in modifying the tagging.

The collected data may be used for testing and training of physicians and the algorithm as described in the exemplary algorithms above. This training enables identification of locations where ablation improvements may be beneficial for improved WACA continuity. System 10 enables analysis of the data and provides access to tools that supply visual analysis to ablations. The data can also be reviewed by other physicians and experts to evaluate the results, and tag the results to improve or correct the tagging to thereby provide improved data understanding.

Figure 20A:
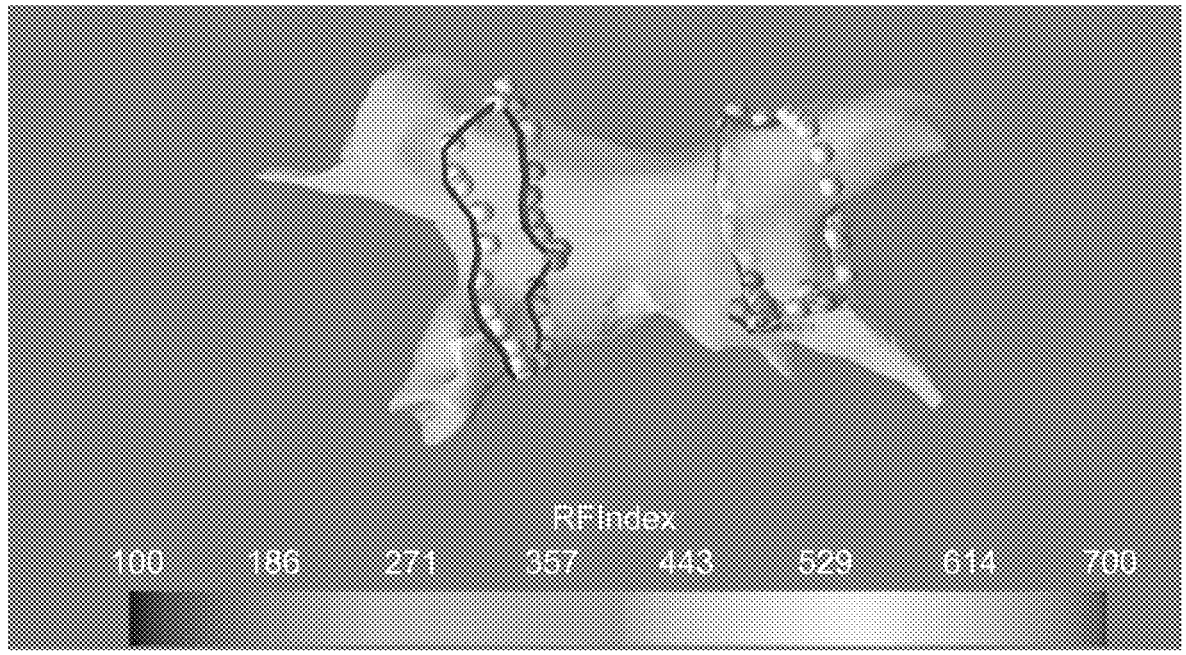
FIG. 20A illustrates a display of the RF index Shurepoint.

In the example WACA analysis tool, there is a display 2000A of the RF index Shure-point illustrated in FIG. 20A. The illustrated display 2000A in FIG. 20A enables the physician to view the values that were presented in a CARTO procedure and acknowledge that these ablation points where used for the WACA. The dots represent the ablations performed and the display illustrates the RF index of the ablations, i.e., the amount of RF energy that is estimated to have been supplied to the tissue, based on delivered energy, contact force and the amount of time the energy was delivered.

Figure 20B:
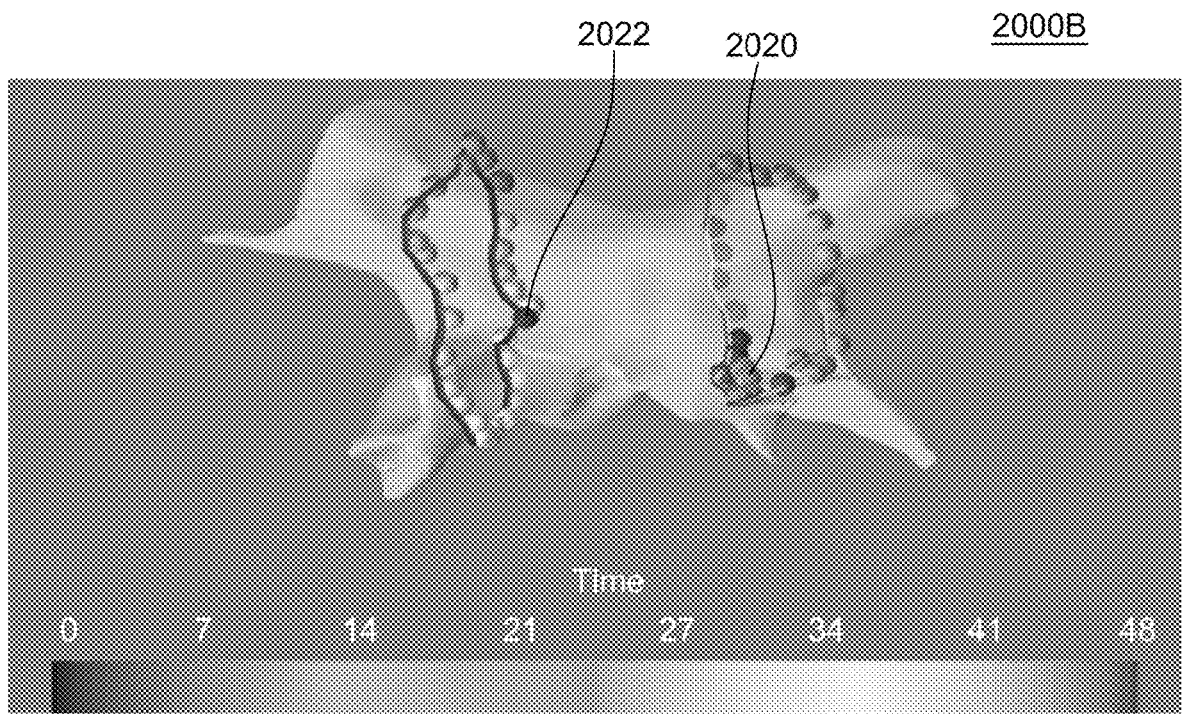
FIG. 20B illustrates a display that identifies the ablation points based in time.

FIG. 20B illustrates a display 2000B that identifies the ablation points based in time. Display 2000B enables the physician to identify the ablations that were used for GAP closing after testing by adenosine stimulation. The physician may view display 2000B to view the two WACA loop times, the first path and the correction path (a few ablation points 2020, and an ablation point 2022). The physician may mark and/or acknowledge each WACA loop, and the correction points. In the situation where a redo is necessary or desired, the physician may be able to perform the redo ablation points on top of the first atrial fibrillation case (not presented on the image).

In display 2000B, the dots represent the time during the procedure that the ablation was created, when the first ablation time is specified as zero, and after, the time in minutes. Display 2000B enables the physician to understand the order of the ablation points during the ablation, and when the procedure was stopped to perform testing. For example, the timing of the loop test, and when the procedure corrected the loop. In the example display 2000B, ablation points 2020 and the associated ablation points represent the correction of the loop.

Figure 20C:
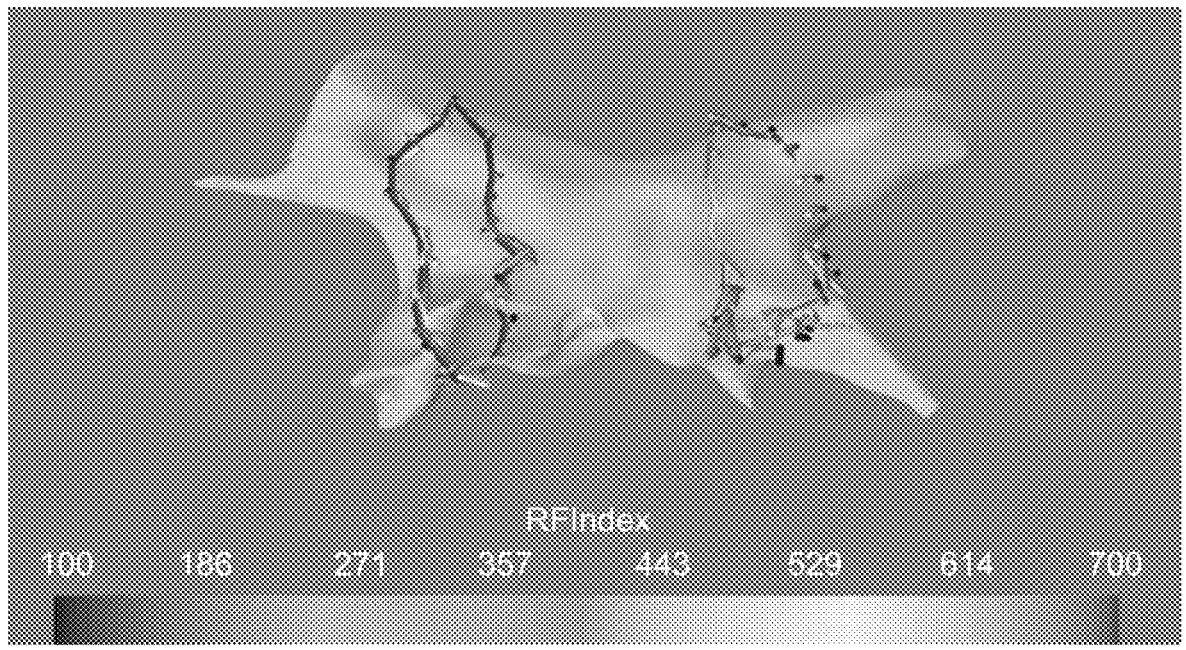
FIG. 20C illustrates a display illustrating the stability view of the RF index detailed representation.

FIG. 20C illustrates a display 2000C illustrating the stability view of the RF index detailed representation. The points are located in space and identify the amount of points near the instability marking. The physician may be able to ascertain the stability of the ablation in each point, and to learn if there is a correlation between the stability and the places that corrected ablation to close the gap was needed.

Display 2000C represents the ablation that was delivered based on micro sites (every millimeter) and the non-ablation points (every session with radius up to 2-5 mm). Display 2000C illustrates that the catheter was not stable. A stable catheter is identified by points where the delivered amount of energy is accumulated to include an RF index in the range of 600 to 700.

Figure 20D:
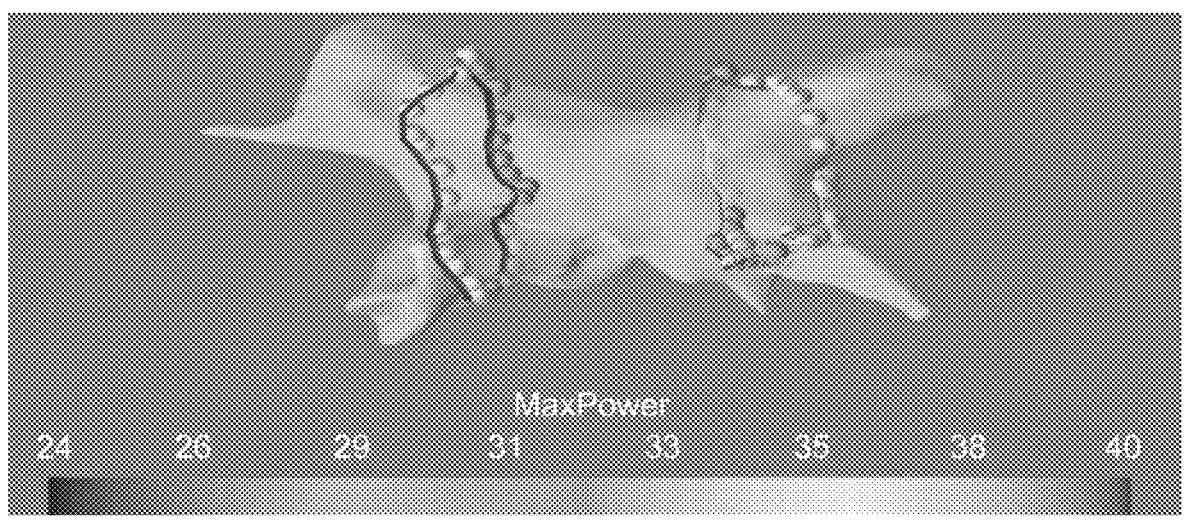
FIG. 20D and FIG. 20E illustrate additional displays that provide display of additional parameters to a using physician.
Figure 20E:
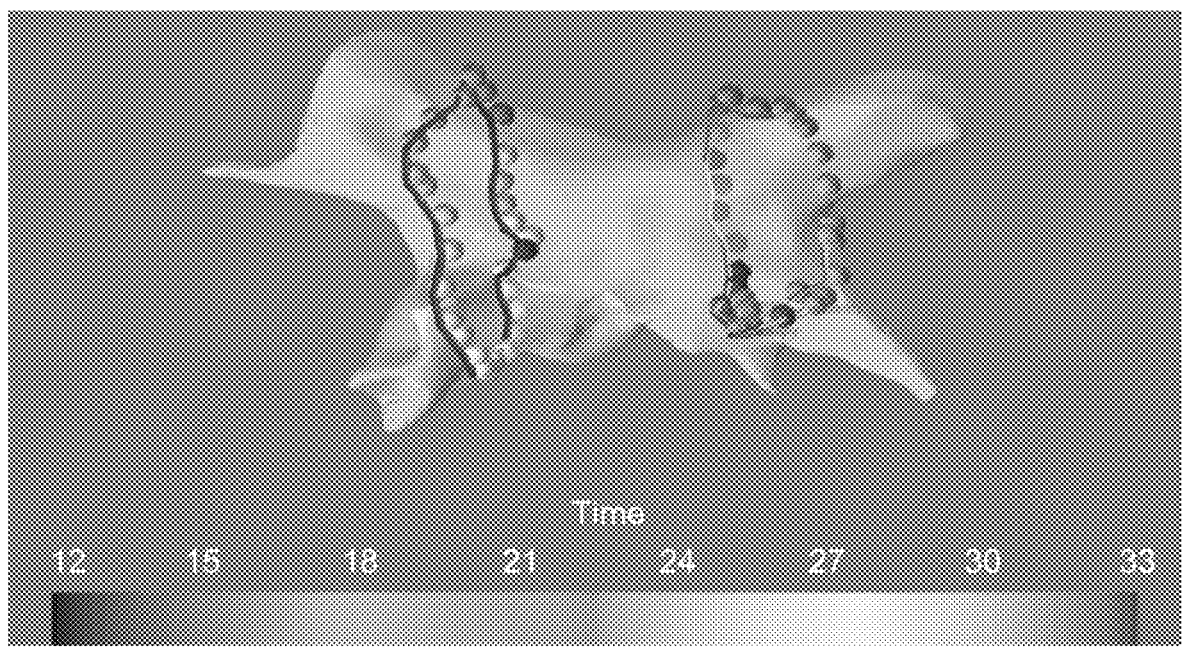

FIG. 20D and FIG. 20E illustrate additional displays 2000D and 2000E respectively, that provide display of additional parameters to a using physician. These additional parameters include impedance drop, base impedance, max temperature, and the like. In addition, the physician can toggle the display to filters by each parameter to improve analysis. The displays 2000D and 2000E present the RF generator delivered energy in watts. The physician may view the displays 2000D and 2000E to understand the energy in both the posttrial wall and the interior wall according to protocol.

Figure 21A:
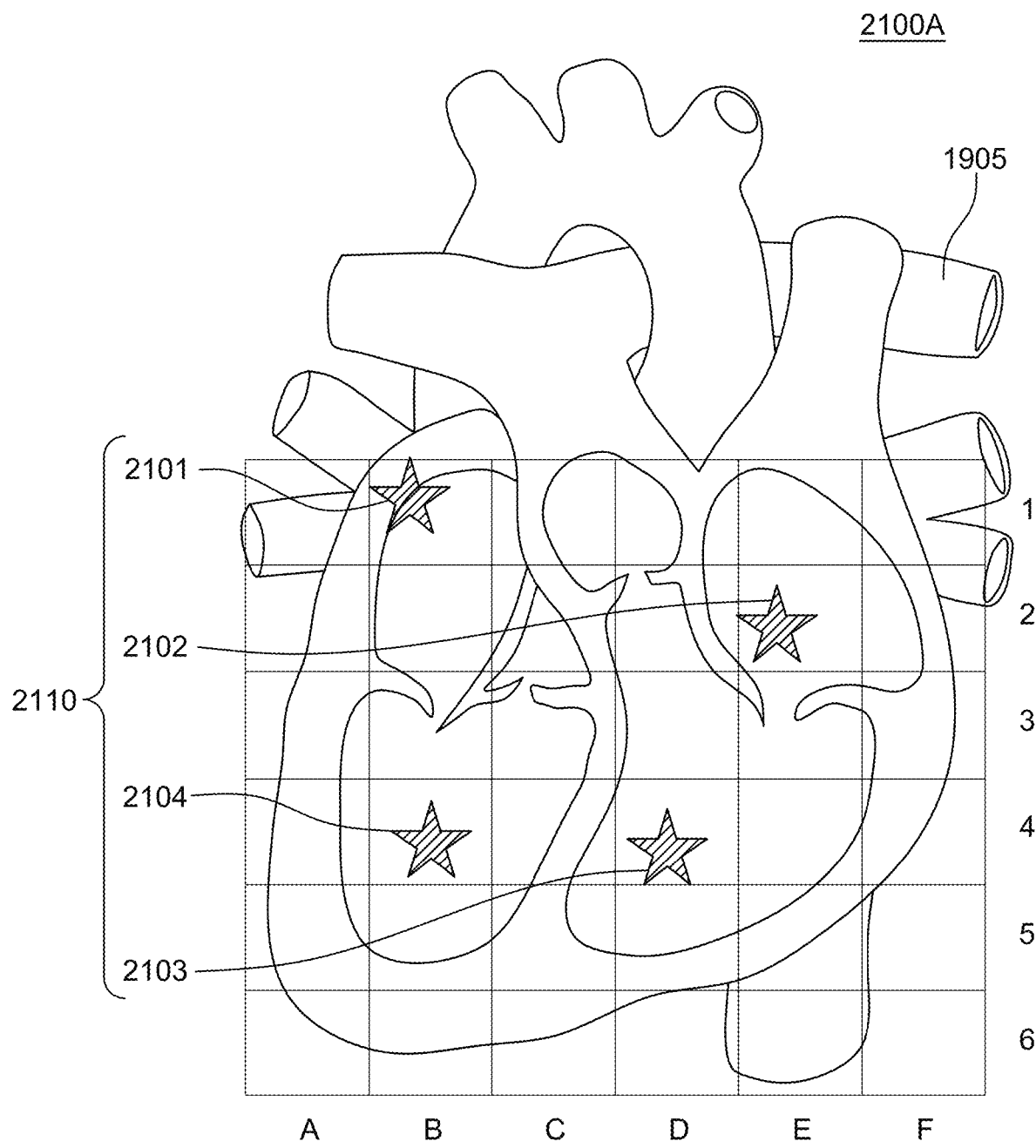
FIG. 21A is a graphical representation of a cardiac ablation treatment plan.

FIG. 21A illustrates a graphical representation 2100A of a cardiac ablation treatment plan 2110. The cardiac ablation treatment plan 2110 identifies a plurality of ablations to be performed on the patient's heart 1905. For example, cardiac ablation treatment plan 2110 is illustrated to include four ablations, identified as first ablation 2101, second ablation 2102, third ablation 2103 and fourth ablation 2104, respectively. Although four ablations are illustrated, a person of ordinary skill in the art would appreciate that any number of ablations are possible. Additionally, the identification of ablations as first, second, third and fourth do not necessarily represent the order that the ablations are performed, instead are intended to delineate the different ablations for ease of understanding.

The cardiac ablation treatment plan 2110 includes a first ablation 2101 that is performed in cell B1 of the horizontal-vertical grid 1910. In addition to location, the cardiac ablation treatment plan 2110 may identify a type, duration and intensity of the first ablation 2101. The cardiac ablation treatment plan 2110 also includes a second ablation 2102 that is performed in cell E2 of the horizontal-vertical grid 1910. A type, duration and intensity of the second ablation 2102 may also be specified in the cardiac ablation treatment plan 2110. The cardiac ablation treatment plan 2110 is illustrated to include a third ablation 2103 that is performed in cell D4 and a fourth ablation 2104 that is performed in cell B4 of the horizontal-vertical grid 1910. A type, duration and intensity of the third ablation 2103 and the fourth ablation 2104 may also be specified in the cardiac ablation treatment plan 2110.

Figure 21B:
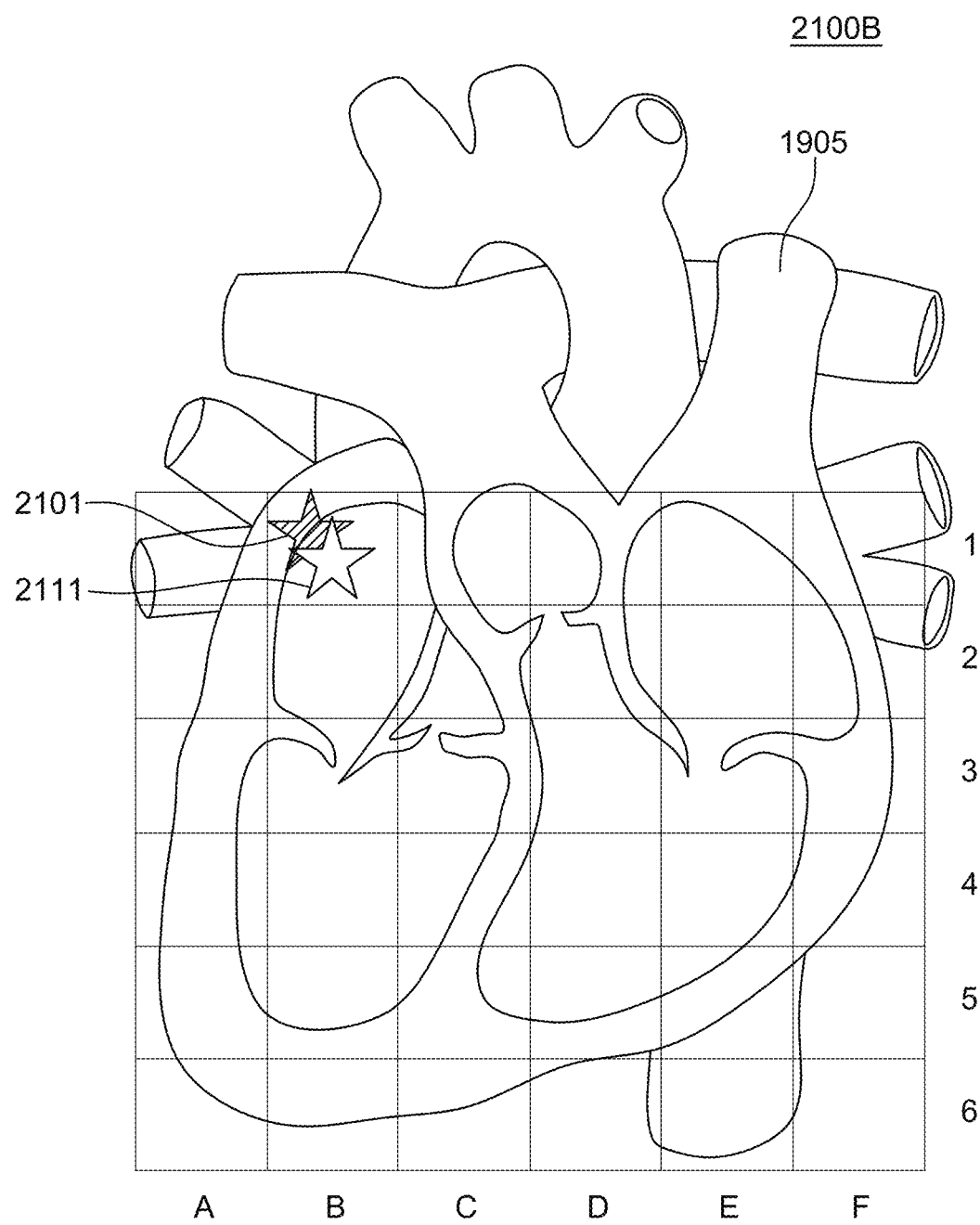
FIG. 21B is a graphical representation of the location of a first ablation performed.

FIG. 21B illustrates a graphical representation 2100B of the location of a first ablation performed according to the cardiac ablation treatment plan 2110. According to cardiac ablation treatment plan 2110, the surgeon should have performed the first ablation 2101. However, the surgeon, in fact, performed the ablation 2111. Ablation 2111 includes a location of that the ablation was actually performed by the surgeon. Ablation 2111 may also include information about the type and the intensity of the ablation actually delivered to the patient's heart 1905.

Figure 21C:
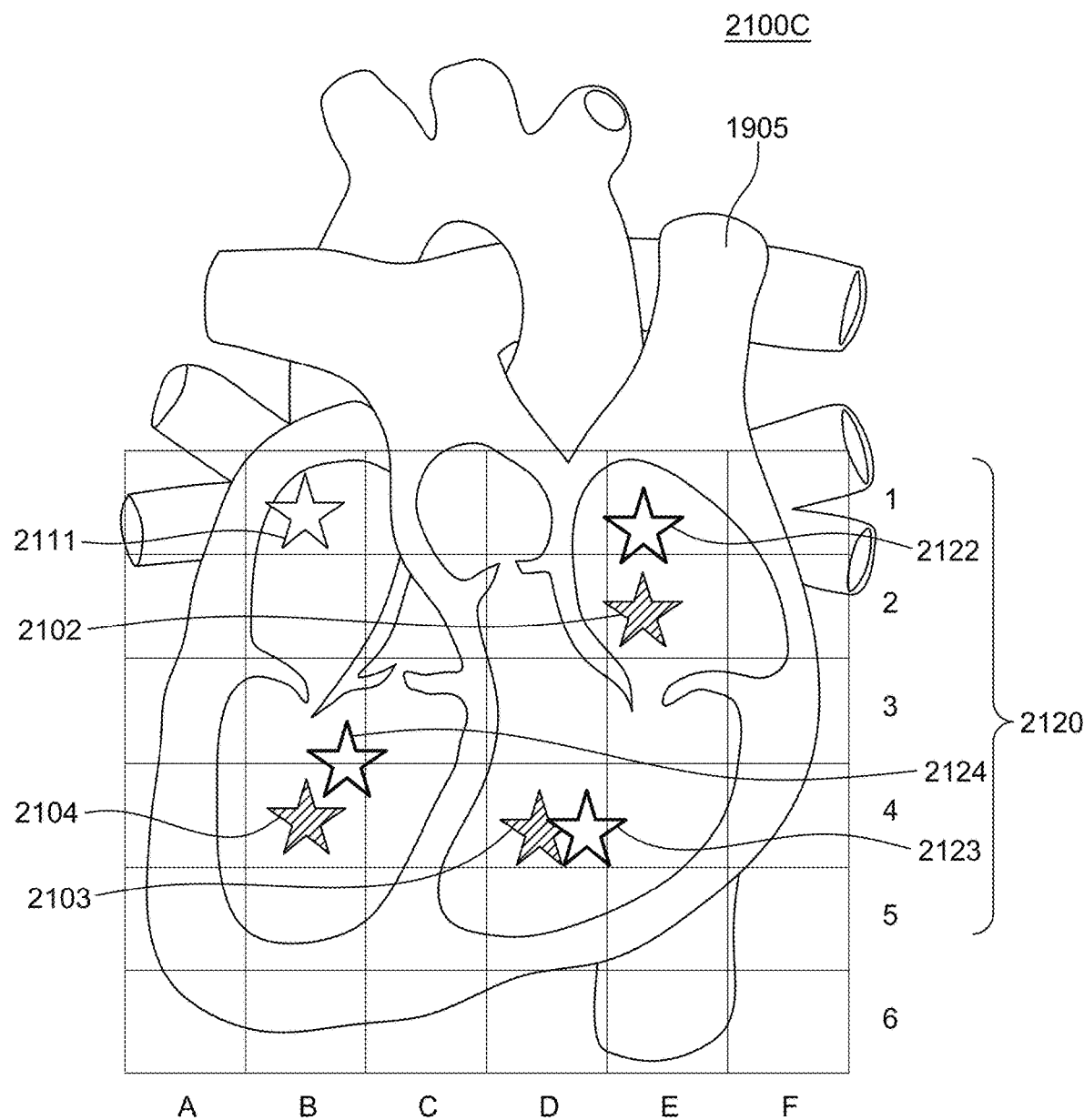
FIG. 21C is a graphical representation of a first revised cardiac ablation treatment plan.

FIG. 21C illustrates a graphical representation 2100C of a first revised cardiac ablation treatment plan 2120. The first revised cardiac ablation treatment plan 2120 is recalculated based on the actual ablation 2111. The revised cardiac ablation treatment plan 2120 includes revised second ablation 2122 as compared to second ablation 2120 from plan 2110, revised third ablation 2123 as compared to third ablation 2103 from plan 2110 and revised fourth ablation 2124 as compared to fourth ablation 2102 from plan 2110. The revised second ablation 2122, revised third ablation 2123 and revised fourth ablation 2124, may each respectively include a location, type, duration and intensity of the respective ablation. In some instances, the first revised cardiac ablation treatment plan 2120 may include a different number of ablations than cardiac ablation treatment plan 2110.

Figure 21D:
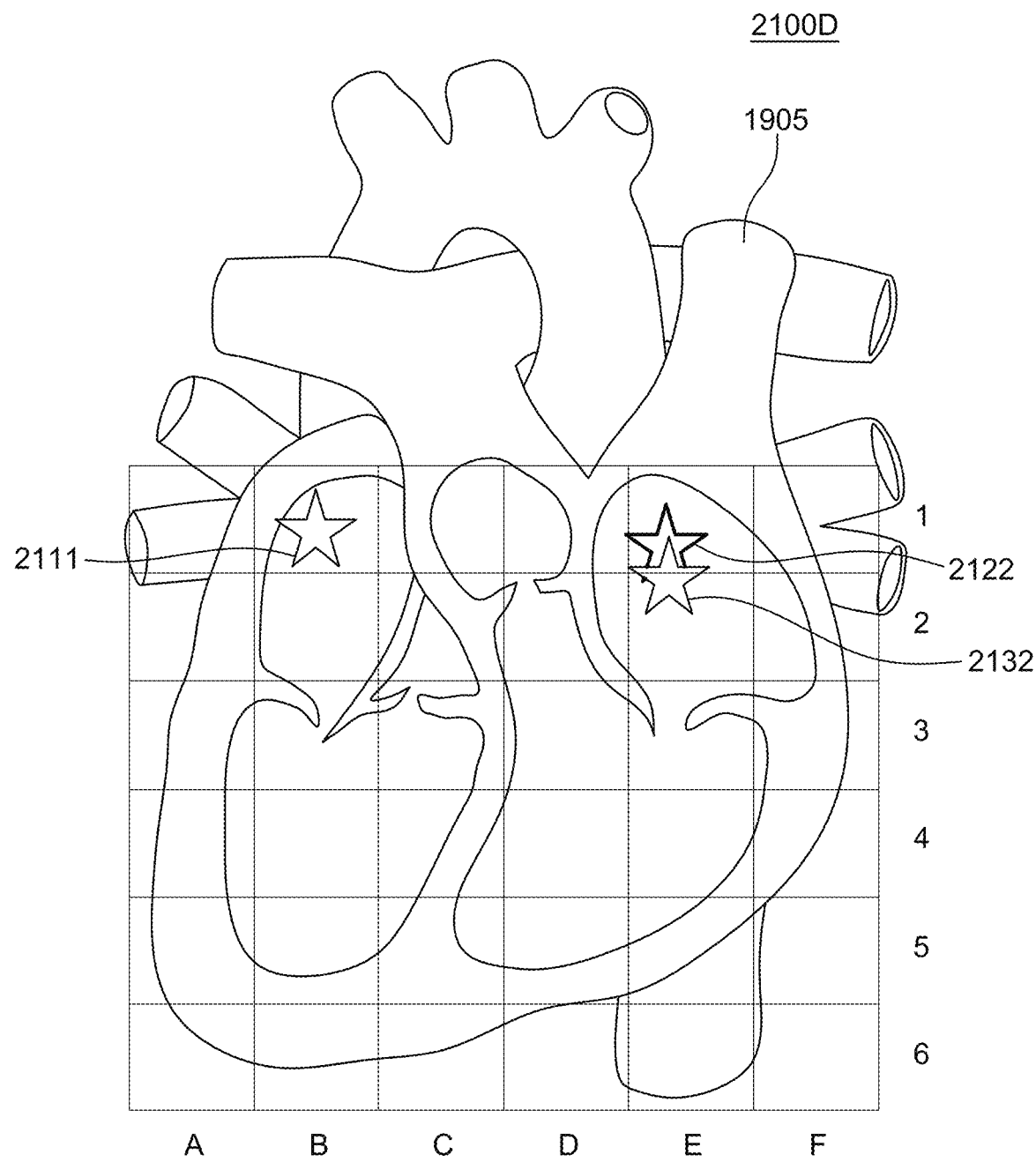
FIG. 21D is a graphical representation of the location of a second ablation.

FIG. 21D illustrates a graphical representation 2100D of the location of a second ablation performed according to the first revised cardiac ablation treatment plan 2120. According to the second revised cardiac ablation treatment plan 2130, the surgeon should have performed the second ablation 2122. However, the surgeon, in fact, performed ablation 2132. Ablation 2132 includes a location of that the ablation was actually performed by the surgeon. Ablation 2132 may also include information about the type and the intensity of the ablation actually delivered to the patient's heart 2105.

Figure 21E:
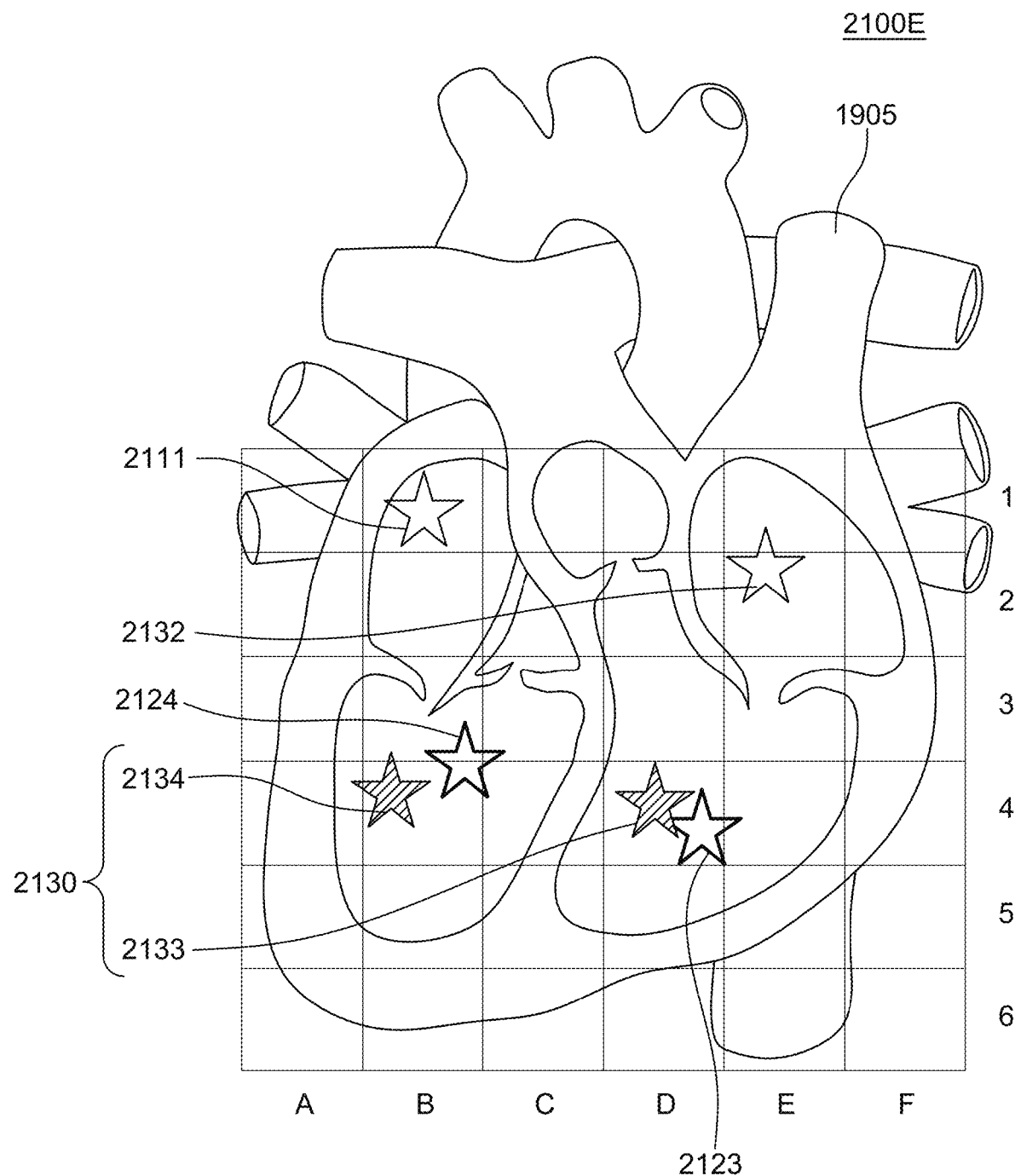
FIG. 21E is a graphical representation of a second revised cardiac ablation treatment plan.

FIG. 21E illustrates a graphical representation 2100E of a second revised cardiac ablation treatment plan 2130. The second revised cardiac ablation treatment plan 2130 is recalculated based on the actual ablation 2111 and actual ablation 2132. The second revised cardiac ablation treatment plan 2130 includes further revised third ablation 2133 as compared to third ablation 2123 of plan 2120 and further revised fourth ablation 2134 as compared to fourth ablation 2124 of plan 2120. The further revised third ablation 2133 and further revised fourth ablation 2144 may each include a location, type, duration and intensity of the respective ablation. In some instances, the second revised cardiac ablation treatment plan 2130 may include a different number of ablations than first revised cardiac ablation treatment plan 2120.

Figure 21F:
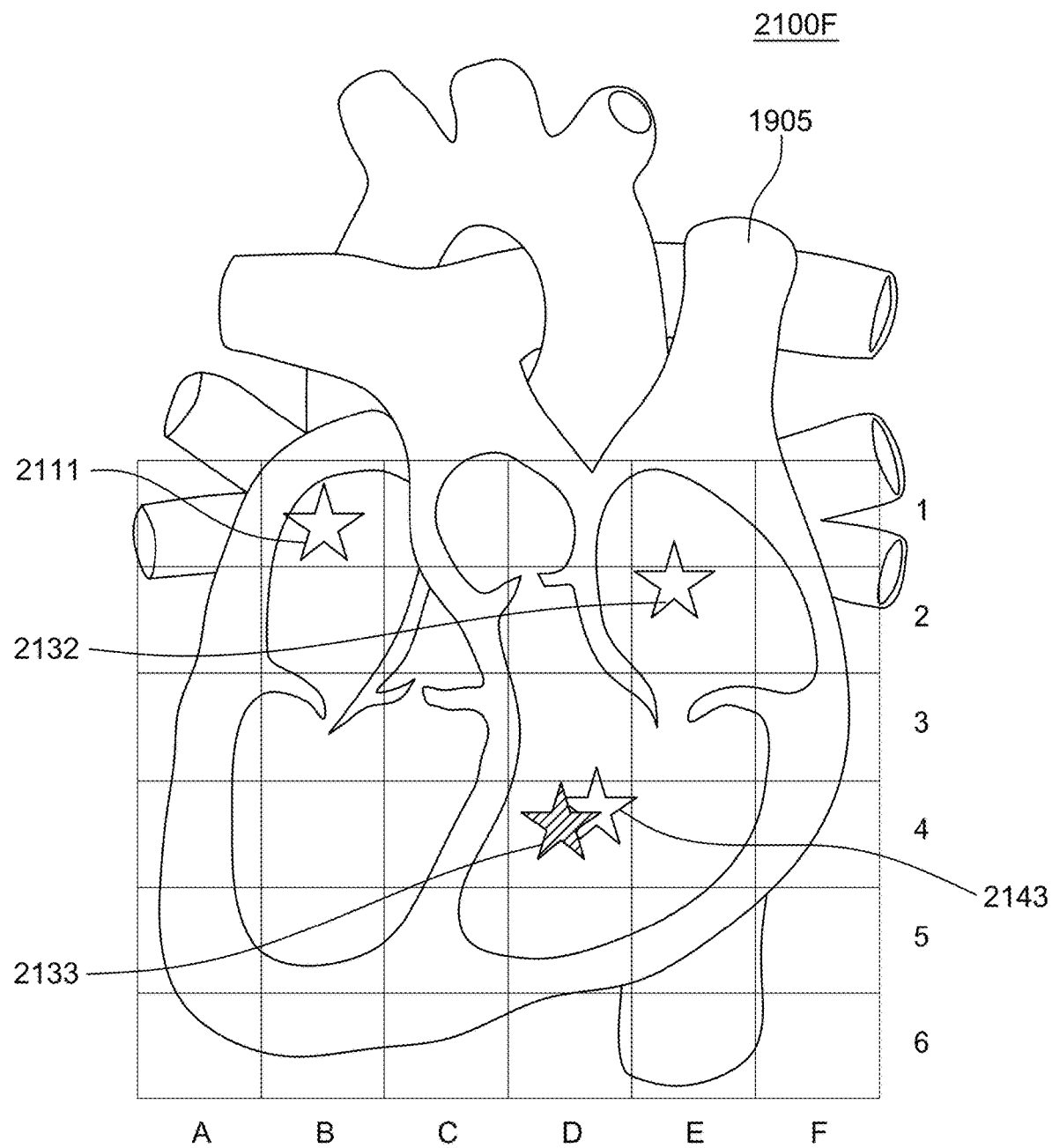
FIG. 21F is a graphical representation of the location of a third ablation.

FIG. 21F illustrates a graphical representation 2100F of the location of a third ablation performed according to the second revised cardiac ablation treatment plan 2130. According to the revised cardiac ablation treatment plan 2130, the surgeon should have performed the third ablation according to 2133. However, the surgeon, in fact, performed ablation 2143. Ablation 2143 includes a location of the ablation that was actually performed by the surgeon. Ablation 2143 may also include information about the type and the intensity of the ablation actually delivered to the patient's heart 1905.

Figure 21G:
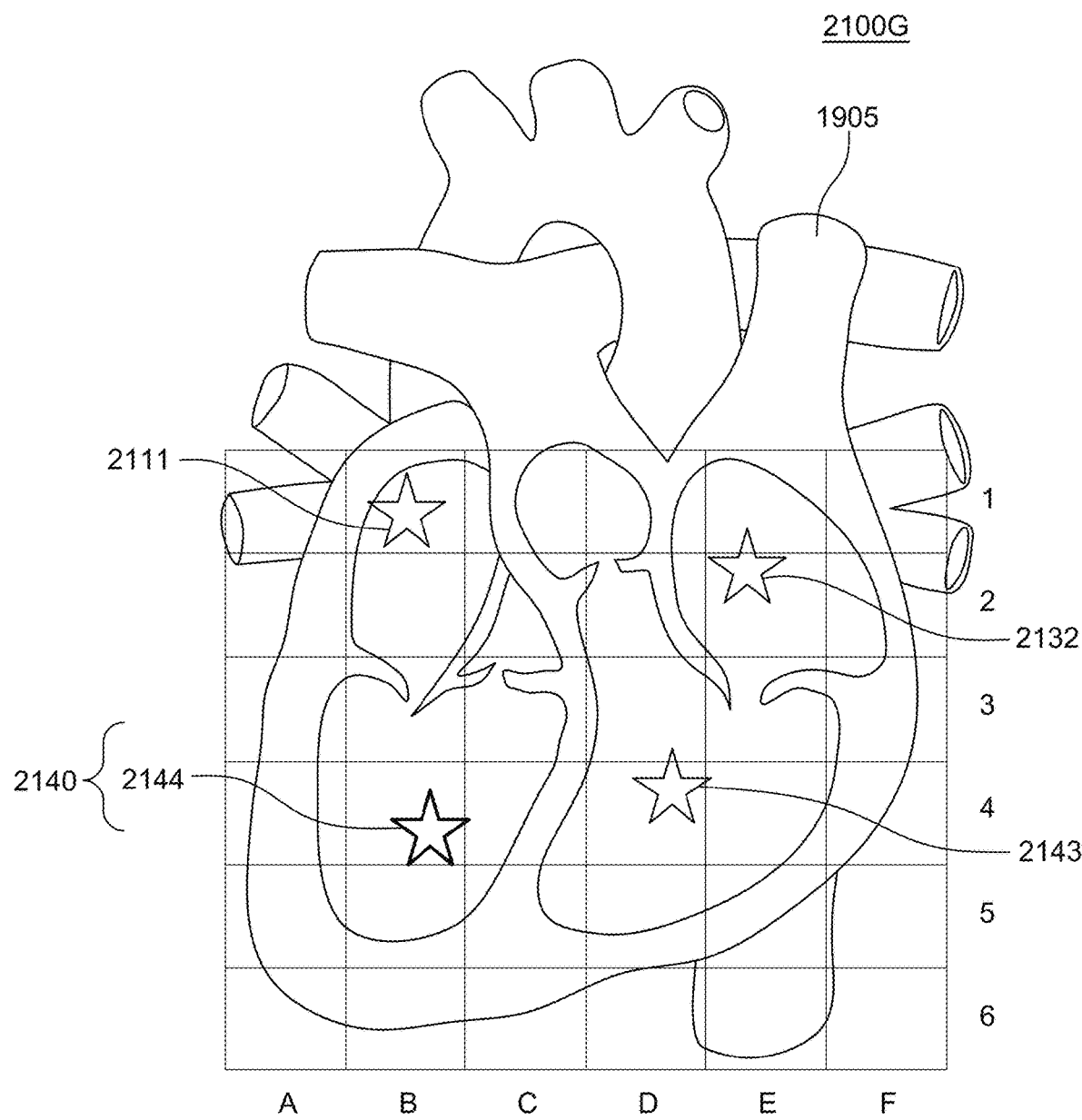
FIG. 21G is a graphical representation of a third revised cardiac ablation treatment plan.

FIG. 21G illustrates a graphical representation 2100G of a third revised cardiac ablation treatment plan 2140. The third revised cardiac ablation treatment plan 2140 is recalculated based on the actual ablation 2111, actual ablation 2132, and actual ablation 2143. The third revised cardiac ablation treatment plan 2140 includes another revised fourth ablation 2144 as compared to the fourth ablation 2134 of plan 2130. The further revised fourth ablation 2144 may include a location, type, duration and intensity of the ablation. In some instances, the third revised cardiac ablation treatment plan 2140 may include a different number of ablations than second revised cardiac ablation treatment plan 2130.

Figure 21H:
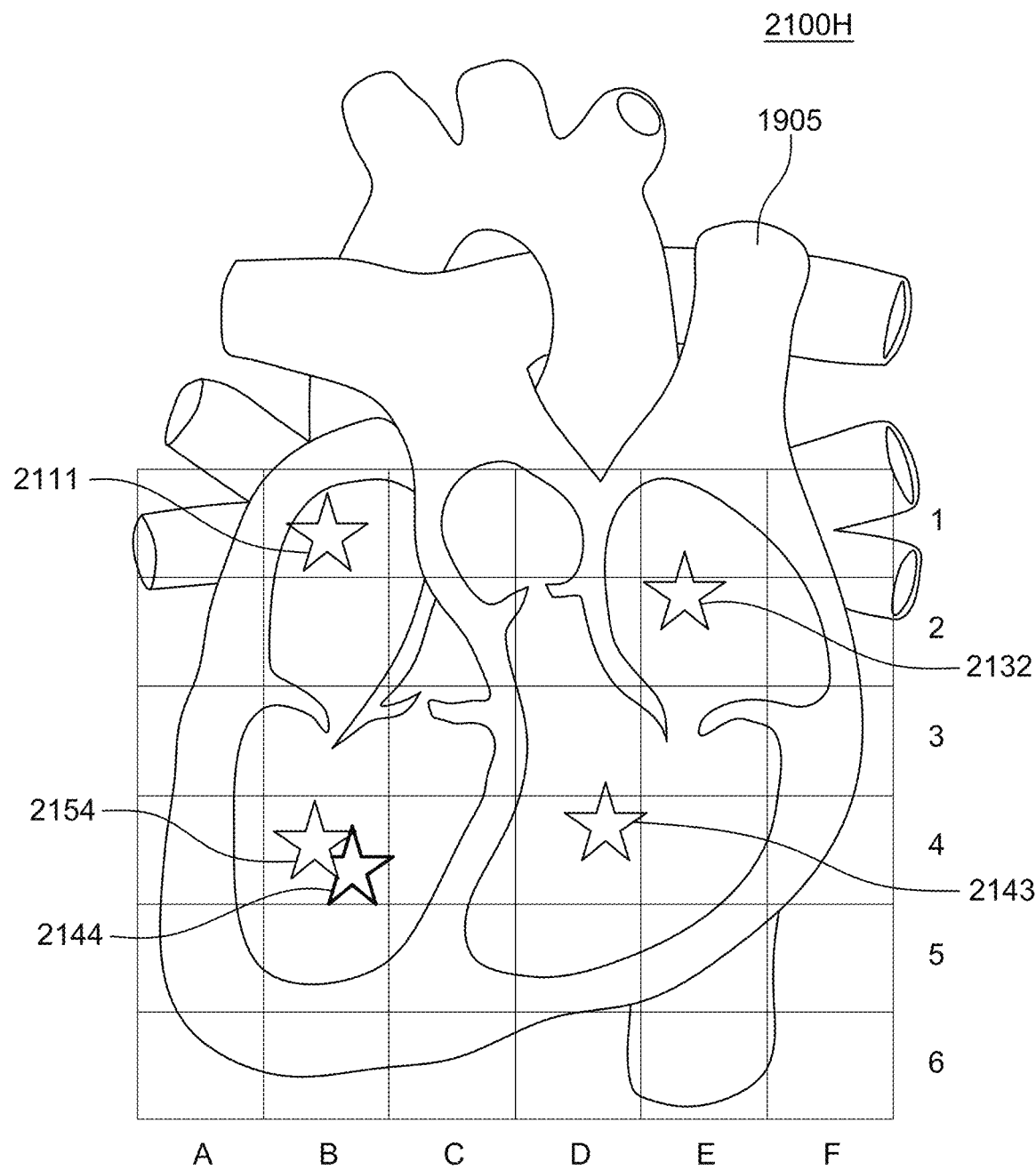
FIG. 21H is a graphical representation of the location of a fourth ablation

FIG. 21H illustrates a graphical representation 2100H of the location of a fourth ablation performed according to the third revised cardiac ablation treatment plan 2140. According to the revised cardiac ablation treatment plan 2140, the surgeon should have performed the third ablation according to 2144. However, the surgeon, in fact, performed ablation 2154. Ablation 2154 includes a location of that the ablation was actually performed by the surgeon. Ablation 2154 may also include information about the type and the intensity of the ablation actually delivered to the patient's heart 1905.

Any of the functions and methods described herein can be implemented in a general purpose computer, a processor, or a processor core. Suitable processors include, by way of example, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), and/or a state machine. Such processors can be manufactured by configuring a manufacturing process using the results of processed hardware description language (HDL) instructions and other intermediary data including netlists (such instructions capable of being stored on a computer-readable media). The results of such processing can be maskworks that are then used in a semiconductor manufacturing process to manufacture a processor which implements features of the disclosure.

Any of the functions and methods described herein can be implemented in a computer program, software, or firmware incorporated in a non-transitory computer-readable storage medium for execution by a general purpose computer or a processor. Examples of non-transitory computer-readable storage mediums include a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs).

It should be understood that many variations are possible based on the disclosure herein. Although features and elements are described above in particular combinations, each feature or element can be used alone without the other features and elements or in various combinations with or without other features and elements.

The invention claimed is:

1. A system for training a surgeon to perform a cardiac ablation, the system comprising:
    a cloud server that includes a database information related to cardiac ablations performed by surgeons with known treatment outcomes; and
    an AR/VR system that is communicatively coupled to the cloud server via a first network, wherein the AR/VR system is configured to:
        receive a plurality of parameters configured for a training ablation related to a patient, the plurality of parameters configured from at least one of the patient medical records or electrical and anatomical data of the patient,
        receive electrical and anatomical data for a virtual patient from the cloud server, wherein the electrical and anatomical data for the virtual patent is determined by comparing the plurality of parameters to the database information and selecting electrical and anatomical data for the virtual patient that meets the comparison and provides the best treatment outcomes of the compared database information,
        create a virtual simulation of a heart of the patient based on the electrical and anatomical data for the virtual patient,
        measure performance of a trainee performing a cardiac ablation procedure on the created virtual simulation by comparing the measured performance with a performance of the surgeon that performed the ablation related to the selected electrical and anatomical data, and
        score the performance of the trainee.

2. The system of claim 1, wherein the cloud server receives the electrical and anatomical data of the heart of the cardiac ablations while a cardiac ablation procedure is performed.

3. The system of claim 1, wherein cardiac ablations include a plurality of ablations, wherein the cloud server receives the electrical and anatomical data of the heart of the patient after each ablation.

4. The system of claim 1, wherein the cloud server is further configured to: receive additional electrical and anatomical data of the heart after the ablation procedure is performed, and generate an ablation score based on the additional electrical and anatomical data.

5. A method for training a surgeon to perform a cardiac ablation, the method comprising:
    receiving a plurality of parameters configured for a training ablation related to a patient, the plurality of parameters configured from at least one of the patient medical records or electrical and anatomical data of the patient;
    receiving electrical and anatomical data for a virtual patient from a cloud server, wherein the electrical and anatomical data for the virtual patent is determined by comparing the plurality of parameters to database information related to cardiac ablations performed by surgeons with known treatment outcomes and selecting electrical and anatomical data for the virtual patient that meets the comparison and provides the best treatment outcomes of the compared database information;
    creating a virtual simulation of a heart of the patient based on the electrical and anatomical data for the virtual patient;
    measuring performance of a trainee performing a cardiac ablation procedure on the created virtual simulation by comparing the measured performance with a performance of the surgeon that performed the ablation related to the selected electrical and anatomical data; and
    scoring the performance of the trainee.

6. The method of claim 5, further comprising receiving the electrical and anatomical data of the heart of the cardiac ablations while a cardiac ablation procedure is performed.

7. The method of claim 5, wherein when the cardiac ablations include a plurality of ablations, the method further comprises receiving the electrical and anatomical data of the heart of the patient after each ablation.

8. The method of claim 5, further comprising receiving additional electrical and anatomical data of the heart after the ablation procedure is performed.

9. The method of claim 5, further comprising generating an ablation score based on additional electrical and anatomical data.

* * * * *

UNITED STATES PATENT AND TRADEMARK OFFICE
CERTIFICATE OF CORRECTION

PATENT NO. : 12,048,487 B2
APPLICATION NO. : 16/864879
DATED : July 30, 2024
INVENTOR(S) : Mati Amit et al.

It is certified that error appears in the above-identified patent and that said Letters Patent is hereby corrected as shown below:

In the Specification

In Column 2, Line 31, delete "ablation" and insert -- ablation. --, therefor.
In Column 3, Line 20, delete "patent" and insert -- patient --, therefor.
In Column 4, Line 23, delete "as well" and insert -- as well as --, therefor.
In Column 5, Line 1, delete "patent's" and insert -- patient's --, therefor.
In Column 5, Line 17, delete "(e.g.," and insert -- e.g., --, therefor.
In Column 5, Line 46, delete "sill" and insert -- skill --, therefor.
In Column 6, Line 19, delete "patents" and insert -- patients --, therefor.
In Column 8, Line 38, delete "addition" and insert -- additional --, therefor.
In Column 9, Line 7, delete "gird" and insert -- grid --, therefor.
In Column 14, Line 5, delete "dimensions" and insert -- dimensions. --, therefor.
In Column 14, Line 12, delete "predicted," and insert -- predictions, --, therefor.
In Column 14, Line 58, delete "pints" and insert -- points --, therefor.
In Column 18, Line 18, delete "local time activation (LAT)" and insert -- local activation time (LAT) --, therefor.
In Column 18, Line 46, delete "CARTO@3" and insert -- CARTO®3 --, therefor.
In Column 21, Line 1, delete "server a" and insert -- server by a --, therefor.
In Column 21, Line 3, delete "@)." and insert -- ®). --, therefor.
In Column 21, Line 36, delete "touch pad," and insert -- touchpad, --, therefor.
In Column 22, Line 18, delete "producer" and insert -- procedure --, therefor.
In Column 22, Line 31, delete "as is" and insert -- as --, therefor.
In Column 24, Line 6, delete "physicians" and insert -- physicians with --, therefor.
In Column 24, Line 7, delete "ones" and insert -- one --, therefor.
In Column 24, Line 40, delete "where" and insert -- were --, therefor.
In Column 27, Line 22, delete "maskworks" and insert -- mask works --, therefor.

In the Claims

In Column 27, Line 59, in Claim 1, delete "patent" and insert -- patient --, therefor.

Signed and Sealed this
Twenty-ninth Day of October, 2024

Katherine Kelly Vidal
*Director of the United States Patent and Trademark Office*

CERTIFICATE OF CORRECTION (continued)
U.S. Pat. No. 12,048,487 B2

In Column 28, Lines 23-24, in Claim 4, delete "generate an......anatomical data." and insert the same on Line 24, as a new sub-point.
In Column 28, Line 34, in Claim 5, delete "patent" and insert -- patient --, therefor.